(12) United States Patent
Iwamura et al.

(10) Patent No.: US 10,262,762 B2
(45) Date of Patent: Apr. 16, 2019

(54) APPARATUS FOR GENERATING FIRST VASCULAR DATA HAVING A TREE STRUCTURE BASED ON ANATOMICAL DATA AND GENERATING SECOND VASCULAR DATA WITHOUT RELYING ON THE ANATOMICAL DATA

(71) Applicants: FUJITSU LIMITED, Kawasaki-shi, Kanagawa (JP); THE UNIVERSITY OF TOKYO, Tokyo (JP)

(72) Inventors: Takashi Iwamura, Sagamihara (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 1285 days.

(21) Appl. No.: 14/447,799

(22) Filed: Jul. 31, 2014

(65) Prior Publication Data
US 2015/0046139 A1    Feb. 12, 2015

(30) Foreign Application Priority Data
Aug. 9, 2013    (JP) .................................. 2013-165855

(51) Int. Cl.
*G16H 50/50* (2018.01)
*G06F 19/00* (2018.01)

(52) U.S. Cl.
CPC ............. *G16H 50/50* (2018.01); *G06F 19/00* (2013.01); *G06F 19/32* (2013.01); *G06F 19/321* (2013.01)

(58) Field of Classification Search
None
See application file for complete search history.

(56) References Cited

U.S. PATENT DOCUMENTS

| 2007/0001879 A1 | 1/2007 | Kaftan et al. |
| 2011/0085701 A1 | 4/2011 | Kitamura |
| 2011/0135172 A1 | 6/2011 | Kitamura |

(Continued)

FOREIGN PATENT DOCUMENTS

| JP | 2007-44488 | 2/2007 |
| JP | 2010-220742 | 10/2010 |
| JP | 2011-98195 | 5/2011 |

(Continued)

OTHER PUBLICATIONS

Smith et al., "An Anatomically Based Model of Transient Coronary Blood Flow in the Heart", SIAM Journal on Applied Mathematics, vol. 62, No. 3, Society for Industrial and Applied Mathematics, Feb. 6, 2002, pp. 990-1018.

(Continued)

*Primary Examiner* — G Steven Vanni
(74) *Attorney, Agent, or Firm* — Staas & Halsey LLP

(57) ABSTRACT

In a vascular data generation apparatus, a processor generates first vascular data based on anatomical statistics data about vessels of an organ. This first vascular data has a tree structure representing a vascular network in the organ. The processor further generates second vascular data representing a plurality of vessels that connect a plurality of nodes in a geometric model of the organ with the vascular network represented by the first vascular data.

8 Claims, 30 Drawing Sheets

(56) References Cited

U.S. PATENT DOCUMENTS

2013/0009958 A1 1/2013 Kitamura

FOREIGN PATENT DOCUMENTS

| JP | 2011-212156 | 10/2011 |
|---|---|---|
| WO | 2013/071219 A1 | 5/2013 |

OTHER PUBLICATIONS

Final Office Action dated Jun. 3, 2016 in U.S. Appl. No. 13/874,904.
Office Action dated Sep. 22, 2014 in U.S. Appl. No. 13/874,904.
Final Office Action dated Apr. 9, 2015 in U.S. Appl. No. 13/874,904.
Office Action dated Oct. 16, 2015 in U.S. Appl. No. 13/874,904.
L. Grinberg et al., "Large-Scale Simulation of the Human Arterial Tree," Clinical and Experimental Pharmacology and Physiology, vol. 36, 2009, pp. 194-205.
H. J. Kim et al., "Patient-Specific Modeling of Blood Flow and Pressure in Human Coronary Arteries," Annals of Biomedical Engineering, Biomedical Engineering Society, vol. 38, Oct. 2010, pp. 3195-3209, 2010.
A. Ullah et al., "Numerical Simulation of Human Blood Flow in Microvessels," *The Nucleus*, , vol. 46, No. 3, 2009, pp. 1-4.
T. Washio et al., "A Parallel Preconditioning for Heart-Coronary Circulation Coupling Simulation," *JSCES Conference Proceedings*, The Japan Society for Computational Engineering and Science (JSCES), vol. 14, May 2009, 4 pages.
S. Cortassa et al., "A computational Model Integrating Electrophysiology, Contraction, and Mitochondrial Bioenergetics in the Ventricular Myocyte," *Biophysical Journal*, Biophysical Society, vol. 91, Aug. 2006, pp. 1564-1589.
W. J. Vankan et al., "Finite-element simulation of blood perfusion in muscle tissue during compression and sustained contraction," *American Journal of Physiology (Heart and Circulatory Physiology)*, American Physiology Society, vol. 273 (vol. 42), Sep. 1997, H1587-H1594 and cover page.
C. C. van Donkelaar et al., "Spatial interaction between tissue pressure and skeletal muscle perfusion during contraction," *Journal of Biomechanics*, Elsevier, vol. 34, Issue 5, May 2001, pp. 631-637.
N. Mittal et al., "Analysis of blood flow in the entire coronary arterial tree," *American Journal of Physiology (Heart and Circulatory Physiology)*, American Physiology Society, vol. 289, Mar. 2005, pp. H439-H446 and cover page.
D. Algranati et al., "Mechanisms of myocardium-coronary vessel interaction," *American Journal of Physiology (Heart and Circulatory Physiology)*, American Physiology Society, vol. 298, Dec. 2009, pp. H861-H873 and cover page.
Murray, "The Physiological Principle of Minimum Work. I. The Vascular System and the Cost of Blood Volume", *Proceedings of the National Academy of Sciences*, published Mar. 1926, vol. 12, No. 3, pp. 207-214, with Table of Contents of *Proceedings of the National Academy of Sciences*, published Mar. 1926, vol. 12, No. 3, 2 pp.
Kamiya et al., "Optical Branching Structure of Vascular Tree", *Seibutsu Butsuri / The Biophysical Society of Japan*, published Mar. 1973, vol. 13, No. 2, pp. 34-39, with National Diet Library Bibliography details of Kamiya et al., "Optical Branching Structure of Vascular Tree", *Seibutsu Butsuri /The Biophysical Society of Japan*, published Mar. 1973, vol. 13, No. 2, 1 pp.
Kassab et al., "Morphometry of pig coronary arterial trees", *American Journal of Physiology—Heart and Circulatory Physiology*, published Jul. 1993, vol. 265, No. 3, pp. H350-H365, with Abstract of Kassab et al., "Morphometry of pig coronary arterial trees", published Jul. 1993, vol. 265, No. 3, 1 pp.
Jiang et al., "Diameter-defined Strahler system and connectivity matrix of the pulmonary arterial tree.", *J. Appl. Physiol.*, published Feb. 1994, vol. 76, No. 2, pp. 882-892, with PubMed Commons Abstract of Jiang et al., "Diameter-defined Strahler system and connectivity matrix of the pulmonary arterial tree.", *J. Appl. Physiol.*, published Feb. 1994, vol. 76, No. 2, 1 pp.
Kassab et al., "Topology and dimensions of pig coronary capillary network", *American Journal of Physiology—Heart and Circulatory Physiology*, published Jul. 1994, pp. vol. 267, No. 36, H319-H325, with Abstract of Kassab et al., "Topology and dimensions of pig coronary capillary network", published Jul. 1994, vol. 267, No. 36, 1 pp.
Kassab et al., "Morphometry of pig coronary venous system", *American Journal of Physiology—Heart and Circulatory Physiology*, published Dec. 1994, vol. 267, No. 36, pp. H2100-H2113, with Abstract of Kassab et al., "Morphometry of pig coronary venous system", published Dec. 1994, vol. 267, No. 36, 1 pp.
Karch et al., "A three-dimensional model for arterial tree representation, generated by constrained constructive optimization", *Computers in Biology and Medicine*, published Jan. 1999, vol. 29 No. 1, pp. 19-38, with Abstract of Karch et al., "A three-dimensional model for arterial tree representation, generated by constrained constructive optimization", *Computers in Biology and Medicine*, published Jan. 1999, vol. 29, No. 1, 1 pp.
Smith et al., "Generation of an Anatomically Based Geometric Coronary Model", *Annals of Biomedical Engineering*, published Jan. 2000, vol. 28, No. 1, pp. 14-25, with PubMed Commons Abstract of Smith et al., "Generation of an anatomically based geometric coronary model", *Annals of Biomedical Engineering*, published Jan. 2000, vol. 28, No. 1, 1 pp.
Kaimovitz et al., "Large-Scale 3-D Geometric Reconstruction of the Porcine Coronary Arterial Vasculature Based on Detailed Anatomical Data", *Annals of Biomedical Engineering*, published Nov. 2005, vol. 33, No. 11, pp. 1517-1535.
Schreiner et al., "Optimized arterial trees supplying hollow organs", *Medical Engineering and Physics*, published Jun. 2006, vol. 28, No. 5, pp. 416-429, PubMed Commons Abstract of Schreiner et al., "Optimized arterial trees supplying hollow organs", *Medical Engineering and Physics*, published Jun. 2006, vol. 28, No. 5, 1 pp.
Kaimovitz et al., "A full 3-D reconstruction of the entire porcine coronary vasculature," *American Journal of Physiology—Heart and Circulatory Physiology*, published Jul. 2010, vol. 299, No. 4, pp. H1064-H1076.
Smith et al., "A computational study of the interaction between coronary blood flow and myocardial mechanics", Physiological Measurement, vol. 25, No. 4, Institute of Physics Publishing, Aug. 2004, pp. 863-877.
Lassila et al., "Geometrical multiscale model of an idealized left ventricle with fluid-structure interaction effects coupled to a one-dimensional viscoelastic arterial network", Proceedings of the ECCOMAS Thematic International Conference on Simulation and Modeling of Biological Flows, Sep. 21-23, 2011, Brussels, Belgium pp. 1-9.
Extended European Search Report dated Mar. 23, 2016 in corresponding European Patent Application No. 13166112.6.
J-PlatPat English Abstract, Publication No. 2011-212156 published Oct. 27, 2011.
J-PlatPat English Abstract, Publication No. 2011-98195 published May 19, 2011.
J-PlatPat English Abstract, Publication No. 2010-220742 published Oct. 7, 2010.
Japanese Office Action dated Jan. 31, 2017 in corresponding Japanese Patent Application No. 2013-165855.
Extended European Search Report dated Dec. 11, 2014 in corresponding European Patent Application No. 14179666.4.
Office Action in Japanese Application No. 2013-165855 dated Jul. 4, 2017.
J-PlatPat English Abstract for Japanese Publication No. 2007-044488, published Feb. 22, 2007.
Office Action for corresponding Japanese Application No. 2013-165855, dated Dec. 5, 2017.
European Office Action dated Aug. 20, 2018 in related European Application No. 13 166 112.6.
U.S. Appl. No. 13/874,904, filed May 1, 2013, Takashi Iwamura, Fujitsu Limited.

141 ANATOMICAL STATISTICS DATA

| Vessel Segment |
| Diameter-defined Strahler Order |
| Vessel Element |
| Diameter, Length |
| Segment-to-Element Ratio S/E |
| Connectivity Matrix: C(m,n) |
| ... |

FINITE ELEMENT MODEL

142a NODE DATA TABLE

| NODE NUMBER | NODE COORDINATES |
|---|---|
| 1 | 0.00 0.00 0.00 |
| 2 | 0.00 0.00 0.50 |
| ⋮ | ⋮ |
| Nnodes | 1.00 2.00 3.00 |

142b MESH DATA TABLE

| MESH NUMBER | NODE NUMBER |
|---|---|
| 1 | 1,2,3,4 |
| 2 | 2,3,4,5 |
| ⋮ | ⋮ |
| Nmesh | Ni,Nj,Nk,Nl |

FIG. 8

143 MACRO MODEL

143a NODE DATA TABLE

| NODE NUMBER | NODE COORDINATES |
|---|---|
| 1 | 0.00 0.00 0.00 |
| 2 | 0.00 0.00 0.50 |
| ⋮ | ⋮ |
| Nnodes | 1.00 2.00 3.00 |

143b VESSEL SEGMENT DATA TABLE

| SEGMENT NUMBER | NODE | ORDER | DIAMETER |
|---|---|---|---|
| 1 | 1,2 | 11 | 0.0030 |
| 2 | 2,3 | 11 | 0.0028 |
| ⋮ | ⋮ | ⋮ | ⋮ |
| Nelem | Nnodes-1,Nnodes | 6 | 0.0002 |

FIG. 9

144 MICRO MODEL

144a NODE DATA TABLE

| NODE NUMBER | NODE COORDINATES |
|---|---|
| 1 | 0.00 0.00 0.00 |
| 2 | 0.00 0.00 0.50 |
| ... | ... |
| Nnodes | 1.00 2.00 3.00 |

144b VESSEL SEGMENT DATA TABLE

| SEGMENT NUMBER | NODE | ORDER | LENGTH | DIAMETER | ELASTICITY COEFFICIENT OF VESSEL WALL | REFERENCE PRESSURE DIFFERENCE | QUANTITY |
|---|---|---|---|---|---|---|---|
| 1 | 1,2 | 5 | 4.5E-4 | 7.1E-5 | 9.7E-10 | 1.0E+4 | 1 |
| 2 | 2,3 | 4 | 1.12E-4 | 4.2E-5 | 4.6E-09 | 9.5E+4 | 8 |
| ... | ... | ... | ... | ... | ... | ... | ... |
| Nelem | Nnodes-1,Nnodes | 1 | 6.0E-5 | 6.5E-6 | 2.6E-09 | 3.0E+04 | 128 |

FIG. 15
CORONARY CIRCULATION DATA
(WITH NO SPATIAL COORDINATES)
44
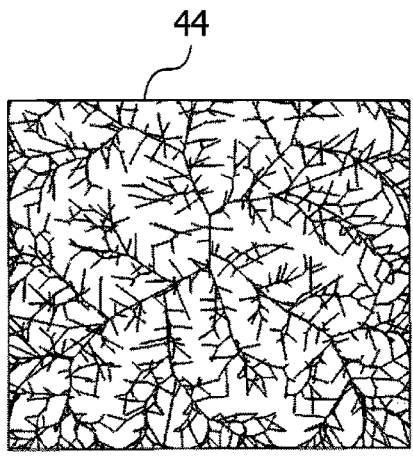
FINITE ELEMENT MODEL
41
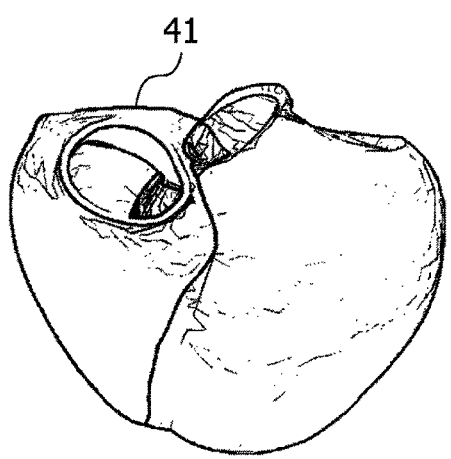
45  MACRO MODEL
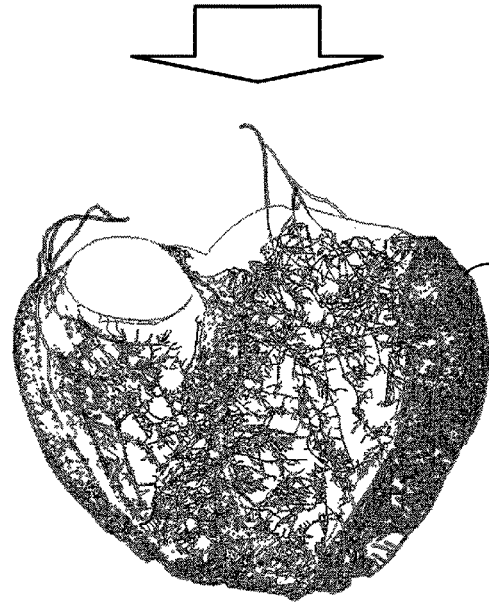

○ End point of existing vessels

⊗ Selected myocardial node

▭ Existing vessels

▬ Vessel added to selected myocardial node

FIG. 29
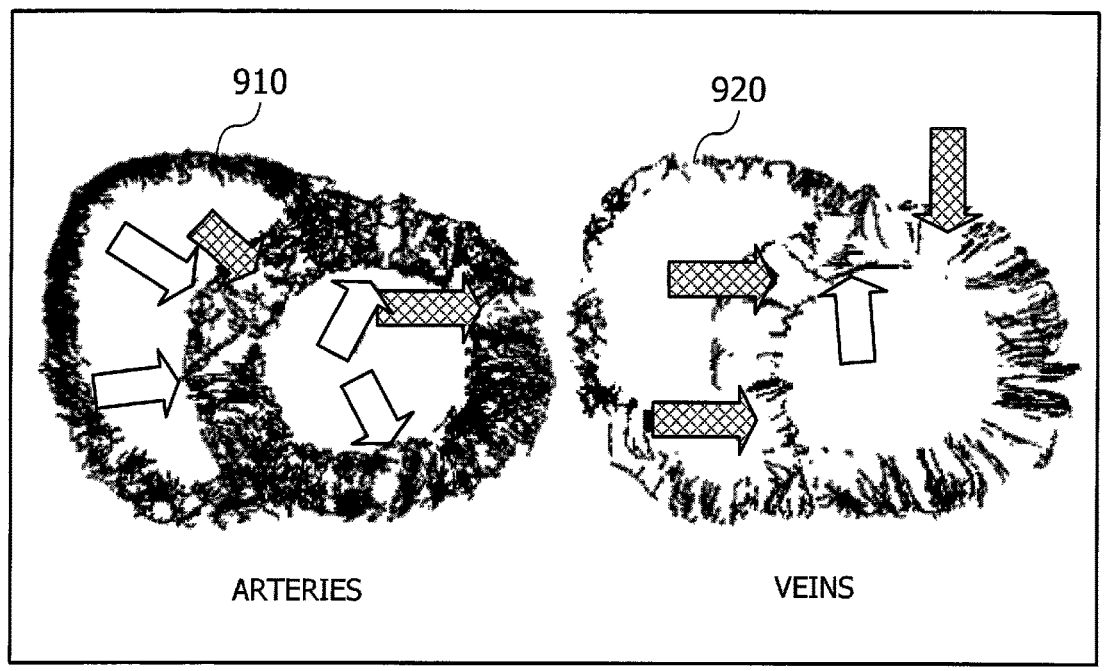
ARTERIES  VEINS
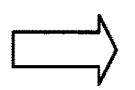 VESSELS RUNNING ON INNER WALL
 LOW DENSITY REGION FIG. 30
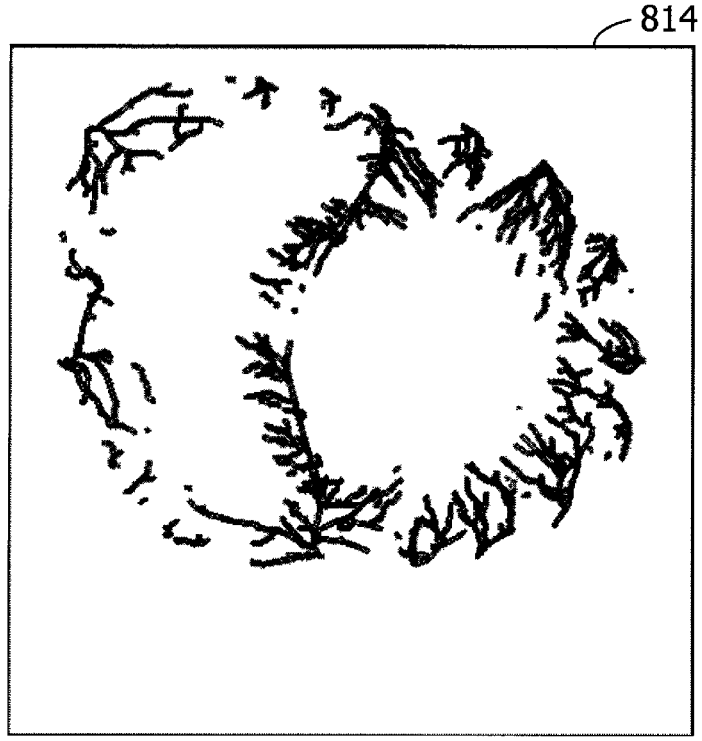
ORDER 7 OR HIGHER
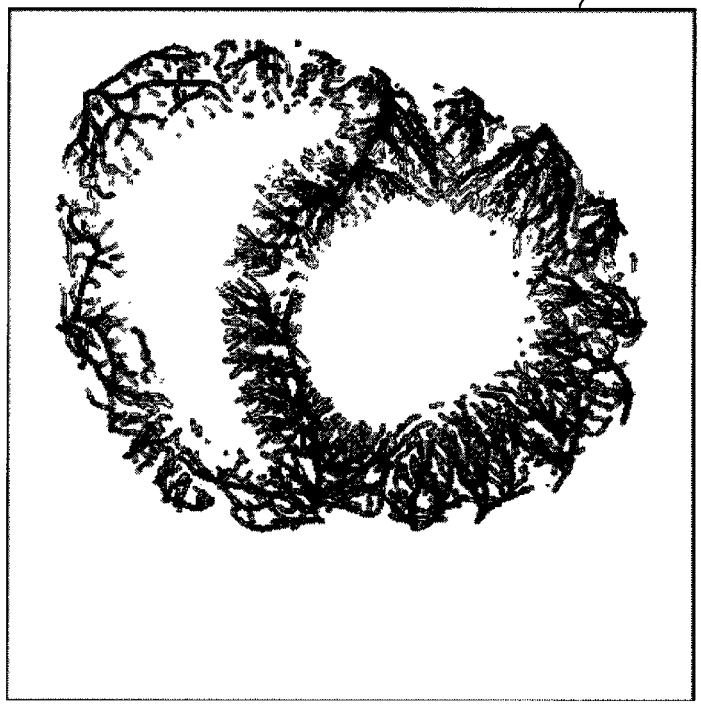
ORDER 6 OR HIGHER

APPARATUS FOR GENERATING FIRST VASCULAR DATA HAVING A TREE STRUCTURE BASED ON ANATOMICAL DATA AND GENERATING SECOND VASCULAR DATA WITHOUT RELYING ON THE ANATOMICAL DATA

CROSS-REFERENCE TO RELATED APPLICATION

This application is based upon and claims the benefit of priority of the prior Japanese Patent Application No. 2013-165855, filed on Aug. 9, 2013, the entire contents of which are incorporated herein by reference.

FIELD

The embodiments discussed herein relate to an apparatus and method for generating vascular data representing a network of blood vessels in an organ.

BACKGROUND

Recent advancement of measurement techniques in the biomedical field has led to a considerable number of findings in the study of proteins, cells, and organs. Those findings are, however, specific to each particular class of objects with a particular relative size or scale. For this reason, the researchers have not necessarily been successful in some study fields such as interactive behavior of cells and organs, which fall into different scale ranges.

The computer technologies, on the other hand, have evolved rapidly toward ever higher performance, and computer simulation tools have taken advantage of such performance enhancements. Simulation-oriented approach has thus been increasingly used in expectation of new discoveries which could not be achieved by conventional measurement-based or experiment-based approaches, while compensating for insufficient accumulation of knowledge in the noted study fields.

The heart of humans is a popular subject of biomedical research using computer simulation techniques. The blood circulation is one of the fundamental mechanisms of life, in which the heart serves as an important organ that sends out blood to the entire body. It is noted that the heart itself also needs a stable supply of blood. Delivery of blood to the heart is done via a network of vessels known as the coronary circulatory system. The pathological conditions derived from abnormalities in the coronary circulation are collectively referred to as ischemic heart diseases. Ischemic heart diseases are mainly caused as a result of coronary arteriosclerosis.

The coronary circulation system has its own form of vessels, which begins with a large vessel running on the myocardial surface, branching into a plurality of distributing vessels with a slight reduction of their diameters. These vessels then run toward the heart chamber (in the transmural direction) while repeating bifurcation with a diameter reduction, thus forming delivering vessels. The coronary artery originates in the aortic sinus of Valsalva and repeats bifurcation and diameter reduction to become small arteries (several 100 µm in diameter) and arterioles (about 200 µm or smaller) until they reach the microcirculation system. At the opposite side of the microcirculation system, coronary venous vessels repeat joining and widening, thus forming venules and small veins extending toward the right atrium. The coronary arteries (and also the coronary veins for this matter) have a tree structure with a single largest vessel at the root and the microcirculatory vessels at the ends of branches. Some portions of coronary veins, however, have a bypass-like structure. The microcirculation system, including arterioles, venules, and capillaries, have a mesh (or network) structure to feed oxygen and nutrients to myocardial cells. The network structure of coronary vessels allows a variety of flows (e.g., parallel flows, counter flows) in the microcirculation system, so as to enable uniform blood supply to the myocardial cells.

The diameter of capillaries ranges from about 5 µm to 6 µm, which is smaller than the size of red blood cells. Red blood cells thus distort their shape during passage through the capillaries. It is the glycocalyx layer in endothelium that permits red blood cells to smoothly travel through vessels while touching their inner wall.

As mentioned, arteriosclerosis is the main cause of ischemic heart diseases, and most studies on arteriosclerosis have been made from the viewpoint of the biochemistry and cell biology. The pathogenesis of ischemic heart diseases is closely related to functional factors such as structure and control of the coronary circulatory system. The heart contraction is considered to give a strong effect on the coronary blood flow. It is known that, with the presence of angina pectoris, ischemia is likely to occur at the endocardial (heart chamber) side of the heart wall, where the tissue pressure increases most significantly. This suggests that the mechanical analysis, in combination with analysis of effects of blood flow (shear stress) related to atheroma formation, is expected to play an important role in study of the pathogenesis of ischemic heart diseases.

Such hemodynamics peculiar to the coronary circulation has drawn the interest of researchers including those who engaged in the basic medical sciences. They have made various kinds of experimental research and have accumulated many findings. One thing to consider here, however, is the fact that the coronary vessels have a wide range of diameters. For example, the diameters of trunks are in the order of millimeters, whereas those of capillaries are in the order of micrometers. That is, the largest coronary vessels are about 1,000 times as thick as the smallest coronary vessels. Another thing to consider is that the heart repeats contraction and relaxation to make a large motion of strokes, which adds significant constraints to realtime observation of coronary blood vessels. These difficulties have hampered deeper investigation of hemodynamics inside the heart wall.

To overcome the above difficulties, the efforts have been made to develop new techniques for experiment and diagnosis. In addition, computer simulation with a coronary circulation model enables observation of coronary vessels without being bound by the technical constraints noted above and is thus expected to be a powerful tool for illuminating the mechanisms of the heart.

The computer simulation uses a computational model as input data. A process of producing a model for simulation is called "modeling." In the case of coronary circulation simulation, the modeling process reproduces, on a computer, a system of coronary vessels on the basis of anatomical and physiological findings about the coronary circulation. More specifically, a coronary circulation model is constructed by successively dividing each vessel segment with a particular diameter and length into multiple vessel segments, or joining multiple vessel segments into a single vessel segment, and then mapping the vessel segments to spatial coordinates of a heart. This modeling technique makes it possible to construct as small vessels as less than 1 mm in diameter, based on mathematical models. These vessels are so small that ordinary computed tomography (CT) scanners or magnetic resonance imaging (MRI) systems are unable to capture their images properly. One of the main purposes of the above studies is to elucidate the coronary hemodynamics and use the findings for prediction of diseases or curative effects. Development of a three-dimensional vascular network model for computer simulation takes part in those efforts.

The modeling methods being studied for coronary circulation simulation are largely divided into two types. One method first produces vascular data having no spatial coordinates, based on detailed anatomical data (e.g., statistics) describing the diameters, lengths, and branching structure of vessels, and then maps it to three-dimensional geometry of the heart. The other method, assuming that in-vivo vessels take a certain optimized form, models a vascular network by applying an optimal model within the geometry of the organ. Either method enjoys the advanced performance of computers to build a large-scale vascular model. The following description gives more specifics about these methods.

(a) Method Based on Anatomical Statistics Data

Input data for this method includes statistics on, for example, the coronary arteries of a swine heart which has been obtained through anatomy. Using the given statistics data together with random numbers generated, the method determines the lengths, diameters, and branching structure (interconnections) of vessels. The resulting vessels are then mapped on the finite element meshes of both ventricles.

(b) Method Based on Optimal Modeling

The method builds a coronary circulation model, without relying on anatomical data, but using an optimal model of vascular networks. The optimization means, in this case, minimizing the sum of energy for making the blood flow (assuming Hagen-Poiseuille flow) and energy for holding the blood (which is proportional to vessel volume). Since each organ has its own specific requirements for the amount of blood flow and the pressure difference for perfusion, the energy for blood flow takes a constant value. A model may then be constructed so as to minimize the volume of vessels under the noted constraints of the amount of blood flow and pressure difference. This model is called a minimum volume model. Based on the minimum volume model, there has been developed another method called the "constrained constructive optimization" (CCO). The CCO assigns flow rate distributions to the geometry of an organ, as well as specific blood pressures at the root and end points of the tree structure of vessels. The CCO then produces new vessel segments at the end points, connects them to other vessel segments, and further moves their connection points so as to minimize the total volume of vessels according to the law of the Hagen-Poiseuille flow.

See, for Example, the Following Documents:

G. S. Kassab, C. A. Rider, N. J. Tang and Y. C. Fung, "Morphometry of Pig Coronary Arterial Trees," American Journal of Physiology, Heart and Circulatory Physiology, 265: H350-H365, 1993

G. S. Kassab, D. H. Lin and Y. C. Fung, "Morphometry of pig coronary venous system," American Journal of Physiology, Heart and Circulatory Physiology, 267: H2100-H2113, 1994

G. S. Kassab and Y. C. Fung, "Topology and dimensions of pig coronary capillary network," American Journal of Physiology, Heart and Circulatory Physiology, 267: H319-H325, 1994

N. P. Smith, A. J. Pullan and P. J. Hunter, "Generation of an anatomically based geometric coronary model," Annals of Biomedical Engineering, vol. 28, pp. 14-25, 2000

B. Kaimovitz, Y. Lanir and G. S. Kassab, "Large-scale 3-D geometric reconstruction of the porcine coronary arterial vasculature based on detailed anatomical data," Annals of Biomedical Engineering, vol. 33(11), pp. 1517-1535, 2005

B. Kaimovitz, Y. Lanir and G. S. Kassab, "A full 3-D reconstruction of the entire porcine coronary vasculature," American Journal of Physiology, Heart and Circulatory Physiology, vol. 299, pp. H1064-H1076, 2010

C. D. Murray, "The physiological principle of minimum work," I. Proceedings of National Academy of Science, 12 207, 1926

A. Kamiya and T. Togawa, "Optimal branching structure of vascular tree," Biophysics, vol. 13 No. 2, pp. 77-81, 1973

R. Karch, F. Neumann, M. Neumann and W. Schreiner, "A three-dimensional model for arterial tree representation, generated by constrained constructive optimization," Computers in Biology and Medicine, vol. 29, pp. 19-38, 1999

W. Schreiner, R. Karch, M. Neumann, F. Neumann, P. Szawlowski and S. Roedler, "Optimized arterial trees supplying hollow organs," Medical Engineering and Physics, vol. 28, pp. 416-429, 2006

Z. L. Jiang, G. S. Kassab and Y. C. Fung, "Diameter-defined Strahler system and connectivity matrix of the pulmonary arterial tree," Journal of Applied Physiology, vol. 76, pp. 882-892, 1994

However, the aforementioned coronary circulation model produced on the basis of anatomical statistics data tends to contain some portions that does not match well with anatomical characteristics of the organ that it represents. For example, a cardiac model produced in this way may have some regions exhibiting an unnaturally low density of vessels, whereas it is known that there has to be a noticeable number of vessels.

The method based on optimal modeling has evolved to be able to produce a partial model of an organ (e.g., a single ventricle with a simplified geometry), but it is not mature enough to reproduce anatomical points as to the entire coronary circulation. For example, the method is still incapable of modeling the left coronary circumflex artery (LCX) and right coronary artery (RCA) running along the boundaries between ventricles and atriums.

The above section has discussed difficulties in producing a coronary circulation model. The researches will, however, encounter similar challenges when modeling a vascular network of other organs.

SUMMARY

As one proposal, there is provided a vascular data generation apparatus including a processor. The processor is configured to perform a procedure including: generating first vascular data based on anatomical statistics data about vessels of an organ, the first vascular data having a tree structure that represents a vascular network in the organ; and generating second vascular data representing a plurality of vessels that connect a plurality of nodes in a geometric model of the organ with the vascular network represented by the first vascular data.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 7 illustrates an exemplary data structure of a finite element model;

FIG. 8 illustrates an exemplary data structure of a macro model;

FIG. 9 illustrates an exemplary data structure of a micro model;

FIG. 15 illustrates an example of how a coronary circulation model (macro model) is produced;

FIG. 29 illustrates an example of coronary circulation models produced for the purpose of comparison; and FIG. 30 illustrates distribution of vessels of different orders.

DESCRIPTION OF EMBODIMENTS

Several embodiments will be described below with reference to the accompanying drawings. These embodiments may be combined with each other, unless they have contradictory features.

(A) First Embodiment

Figure 1:
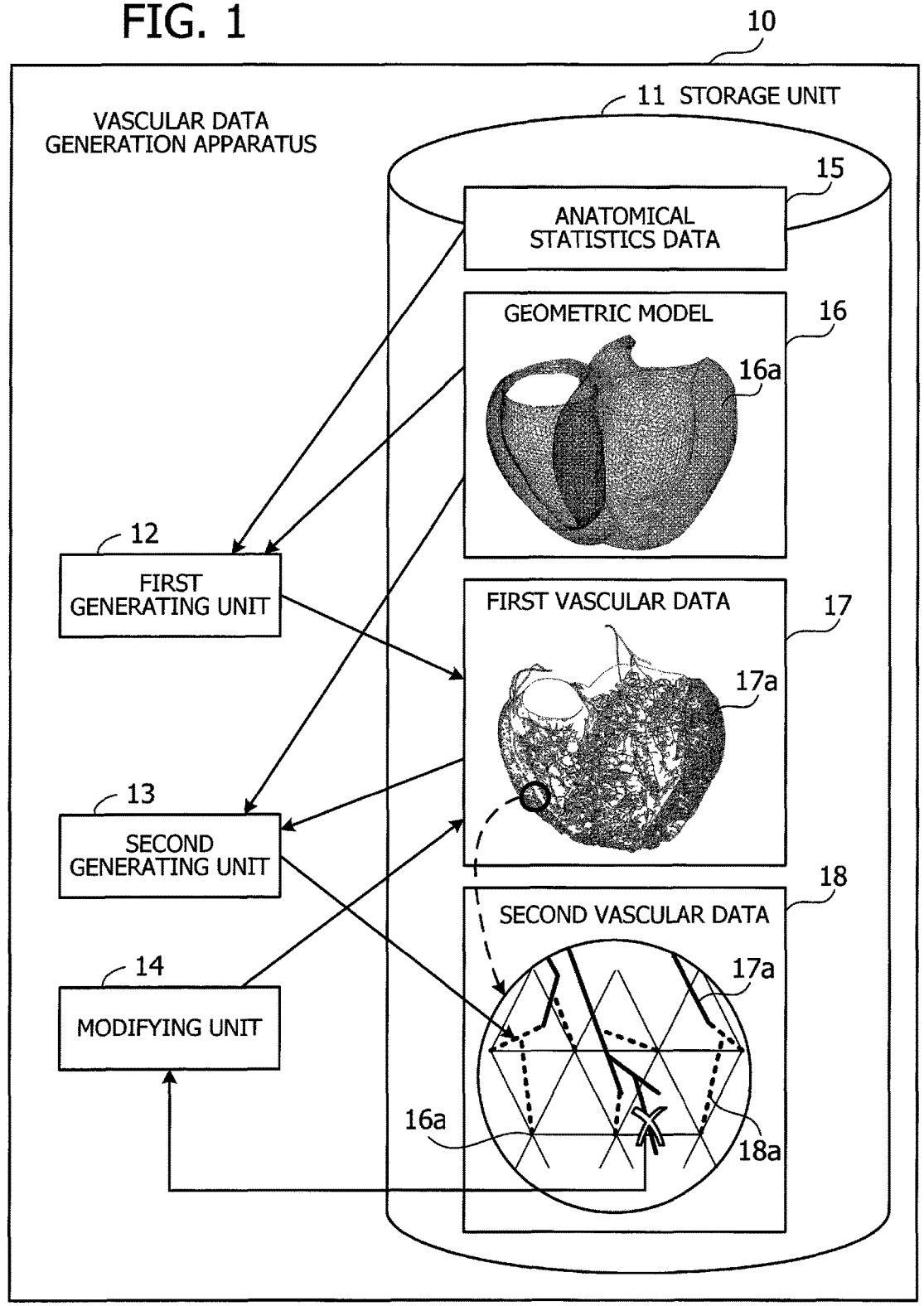
FIG. 1 illustrates an example of a functional structure of a vascular data generation apparatus according to a first embodiment.

FIG. 1 illustrates an example of a functional structure of a vascular data generation apparatus according to a first embodiment. This vascular data generation apparatus 10 includes a storage unit 11, a first generating unit 12, a second generating unit 13, and a modifying unit 14.

The storage unit 11 stores anatomical statistics data 15, a geometric model 16, first vascular data 17, and second vascular data 18. The anatomical statistics data 15 is statistics data representing anatomical characteristics (e.g., diameters, lengths, and branching structure of vessels) of an animal organ such as the heart of humans. The geometric model 16 is a set of data that defines a three-dimensional shape of the organ by using a plurality of nodes 16a. For example, the geometric model 16 is organized as a collection of tetrahedrons that divide the organ into meshes, where the nodes 16a are the vertices of these tetrahedral elements of the geometric model 16. The first vascular data 17 is a set of tree-structured data representing a vascular network 17a in the organ. The second vascular data 18 is a set of data representing vessels that connect the vascular network 17a of the first vascular data 17 with the nodes 16a in the geometric model 16.

The first generating unit 12 generates first vascular data 17 representing a vascular network 17a in the organ of interest on the basis of given anatomical statistics data 15 of vessels in that organ. For example, the first generating unit 12 generates a vascular network 17a including branching of vessels, as well as thickness (i.e., diameter or radius) and length of each vascular portion, based on the anatomical statistics data 15. Here the anatomical statistics data 15 includes no information about spatial coordinates of vessels. For example, the generation of a vascular network 17a begins at the root of its tree structure and proceeds toward the end of each branch so that the largest blood vessel at the root forks into smaller vessels. The first generating unit 12 then determines the coordinate positions of nodes, such as bifurcation points and extreme ends of vessels, by mapping the vascular network 17a into the geometric model 16, assuming that the geometric model 16 is placed in a certain virtual space. The first generating unit 12 stores the generated first vascular data 17 in the storage unit 11.

The second generating unit 13 generates second vascular data 18 representing a plurality of blood vessels that connect each node 16a in the geometric model 16 to the vascular network 17a represented by the first vascular data 17. For example, the second generating unit 13 extends vessels from the plurality of nodes 16a toward the vascular network 17a. The second generating unit 13 stores the generated second vascular data 18 in the storage unit 11. The extended vascular network (17a plus 18a) represented by the first vascular data 17 and second vascular data 18 is then subjected to optimization based on a predetermined evaluation function. The second generating unit 13 optimizes the first vascular data 17 and second vascular data 18 so that the resulting network will be valued as higher as possible. For example, the evaluation function may be designed to increase the rating of a vascular network as its total blood volume becomes smaller. The optimization process actually changes, for example, some bifurcation points of vessels in the network, as well as the lengths and diameters of some vessels.

The modifying unit 14 further modifies the first vascular data 17 by removing some end portions of the vascular network 17a that have no additional vessels connected in the second vascular data 18.

In operation of the above vascular data generation apparatus 10, the first generating unit 12 generates first vascular data 17 based on anatomical statistics data 15. This first vascular data 17, however, may partly disagree with the actual form of blood vessels in the real organ. For example, a part of the organ represented by the geometric model 16 may exhibit an unnaturally coarse distribution of vessels, compared with the actual vessel density observed in a real human heart.

The second generating unit 13 thus generates second vascular data 18 representing a plurality of vessels 18a that connect a plurality of nodes 16a in the geometric model 16 with the vascular network 17a represented by the first vascular data 17. Here the geometric model 16 in FIG. 1 is made up of a plurality of tetrahedral elements, where the vertices of each tetrahedron are the nodes of the geometric model 16. The second generating unit 13 has produced second vascular data 18 representing additional vessels 18a (broken lines) each connecting one of the nodes 16a with some point on the vascular network 17a (solid lines).

Even after the second vascular data 18 is completed, some terminal vessels of the vascular network 17a still have no vessels 18a connected. These terminal vessels in the vascular network 17a could be inefficient in terms of the blood delivery, and such inefficient vessels often disagree with the actual form of blood vessels in a real organ. The modifying unit 14 thus modifies the first vascular data 17 by pruning these unsuitable portions of the vascular network 17a (i.e., terminal vessels having gained no additional vessels in the second vascular data 18).

The above processing has produced first vascular data 17 and second vascular data 18 representing an extended vascular network formed from properly routed vessels. Even if the initial vascular network of the first vascular data 17 had a low-density region of vessels, the second generating unit 13 would populate that region with additional vessels in the second vascular data 18. This feature prevents the simulation model from containing regions with unnaturally coarse vessels. Further, the first vascular data 17 is modified to remove terminal vessels in the vascular network 17a when they have no additional vessels of the second vascular data 18. The final vascular network is provided as the first vascular data 17 and second vascular data 18, with no unsuitable vessels in terms of the efficiency of blood delivery.

As described above, the first generating unit 12 generates first vascular data 17 based on anatomical statistics data 15. More specifically, the first generating unit 12 achieves this by modeling the vessels as observed in medical images and then connecting vessels generated from the anatomical statistics data 15 to end points of the former vessels. The origin of the former vessels is medical images, and these vessels are treated as having fixed diameters and lengths. For example, medical images are captured by scanning a particular patient's organ. The first generating unit 12 generates vascular data of the patient, preserving the patient-specific condition of vessels.

The second generating unit 13 may use an evaluation function that gives different ratings depending on the difference of blood pressures between one end point of the vascular network in question and an upstream point of a vessel connected to that end point. Specifically, when the upstream point has a higher blood pressure than the end point, the evaluation function increases the rating as the pressure difference becomes larger. When the upstream point has a lower blood pressure than the end point, the evaluation function decreases the rating as the pressure difference between the two points becomes larger. The use of this evaluation function prevents the vascular network from having higher blood pressures at its end points than the upstream points of vessels connected to the end points.

The second generating unit 13 may use another evaluation function that highly values a vessel in the second vascular data 18 when its length is longer than its diameter. This evaluation function may be used to adjust the connection point of each new vessel in the second vascular data 18 when connecting it to existing vessels represented by the first vascular data 17, so as to avoid adding a new vessel to existing bifurcation points in the vascular network.

The second generating unit 13 may use yet another evaluation function that is based on the flow rate of blood in the vessels, where the vessels will be given a larger amount of blood flow as they are connected to nodes closer to the inner surface of the organ. This feature enables evaluation of a vascular network, taking into consideration the actual distribution of blood flows in the organ.

The second generating unit 13 sequentially selects each node contained in a given geometry model and determines where to connect a new vessel produced at the selected node, as well as how long and thick the new vessel will be. In this node selection, the nodes closer to the outer surface of the organ are given higher probabilities of selection. This setup of probabilities results in a network of vessels routed from the outer surface toward the inner surface of the organ. The produced vessels in the model run in appropriate directions similar to those in a real organ.

The above-described first generating unit 12, second generating unit 13, and modifying unit 14 may be implemented as, for example, functions executed by a processor in the vascular data generation apparatus 10. Similarly the storage unit 11 may be implemented as a memory in the vascular data generation apparatus 10.

It is noted that the lines interconnecting the functional blocks in FIG. 1 represent some of their communication paths. The person skilled in the art would appreciate that there may be other communication paths in actual implementations.

(B) Second Embodiment

A second embodiment will now be described below. The second embodiment enables execution of a coronary circulation simulation with a parallel computing system formed from a plurality of computing nodes each having one or more multi-core CPUs.

For computer simulation of coronary circulation, the second embodiment manages a coronary circulation model in two parts called "macro model" and "micro model." A macro model is a vascular network model formed from large coronary arteries and large coronary veins. A micro model is another class of vascular network model, which represents thinner vessels than those of in the macro model. To enhance the efficiency of simulation, the second embodiment employs a parallel computing system and executes multiple micro-model computations in a parallel fashion.

Figure 2:
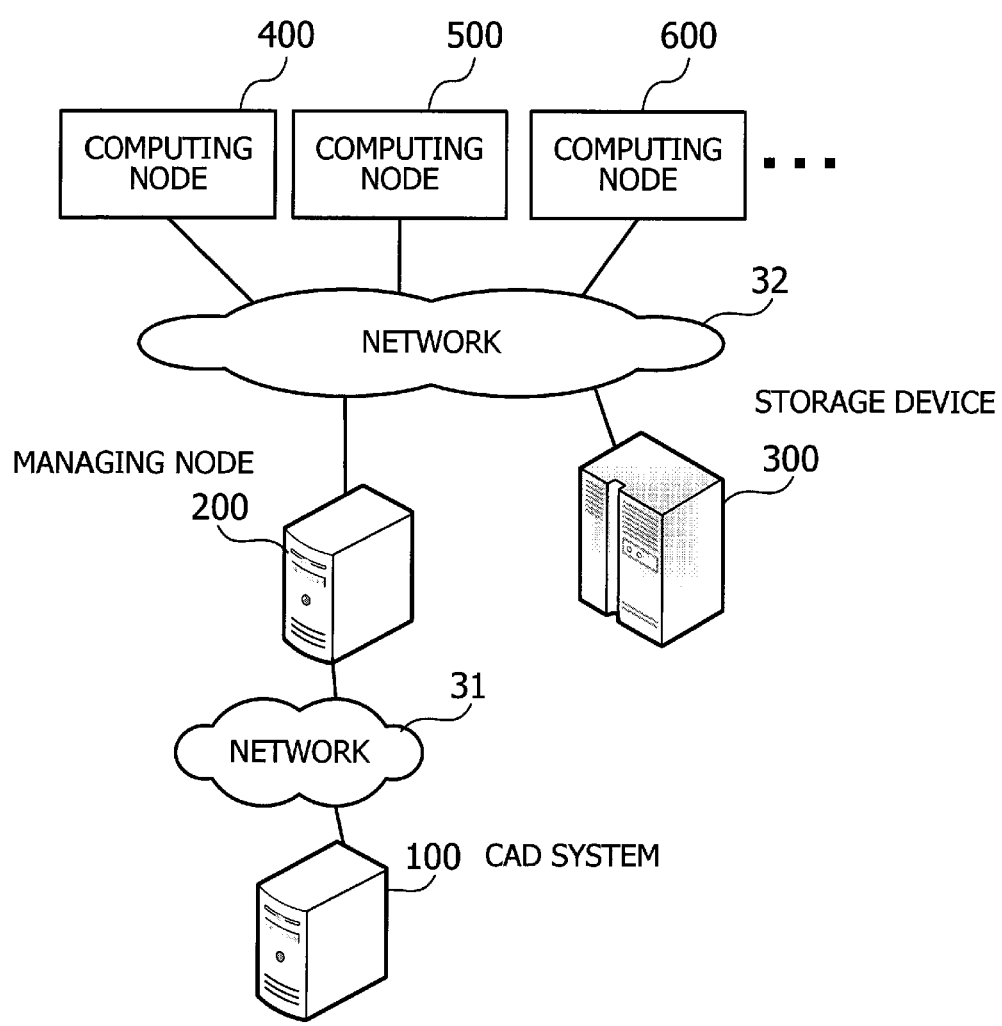
FIG. 2 illustrates an exemplary system configuration according to a second embodiment.

FIG. 2 illustrates an exemplary system configuration of the second embodiment. This system includes a computer-aided design (CAD) system 100 that permits the user to perform modeling of the three-dimensional structure of a heart, including its coronary vessel network. The CAD system 100 is linked to a managing node 200 via a network 31. The CAD system 100 sends a three-dimensional structure model and a coronary vessel network model to this managing node 200 and issues a command to the managing node 200 to execute a coronary circulation simulation on these models.

The managing node 200 is connected to a storage device 300 and a plurality of computing nodes 400, 500, 600, . . . via another network 32. The managing node 200 uses the storage device 300 to store the three-dimensional structure model and coronary vessel network model received from the CAD system 100. Upon receipt of a command from the CAD system 100 for execution of a coronary circulation simulation, the managing node 200 dispatches jobs to computing nodes 400, 500, 600, . . . for the requested simulation. During the course of this job dispatching process, the managing node 200 informs each computing node of, for example, the location of model data, programs for the job execution, and various parameters used in their jobs.

The storage device 300 includes a plurality of hard disk drives to store data of models that the user has produced with the CAD system 100. The storage device 300 may include solid state drives (SSD) instead of, or together with the hard disk drives. These drives may be configured to use the Redundant Array of Independent Disks (RAID) technology.

The computing nodes 400, 500, 600, . . . run in parallel to execute a coronary circulation simulation in accordance with commands from the managing node 200. Since multi-core CPUs are used in these computing nodes 400, 500, 600, . . . , each individual computing node is capable of executing multiple processes concurrently.

Figure 3:
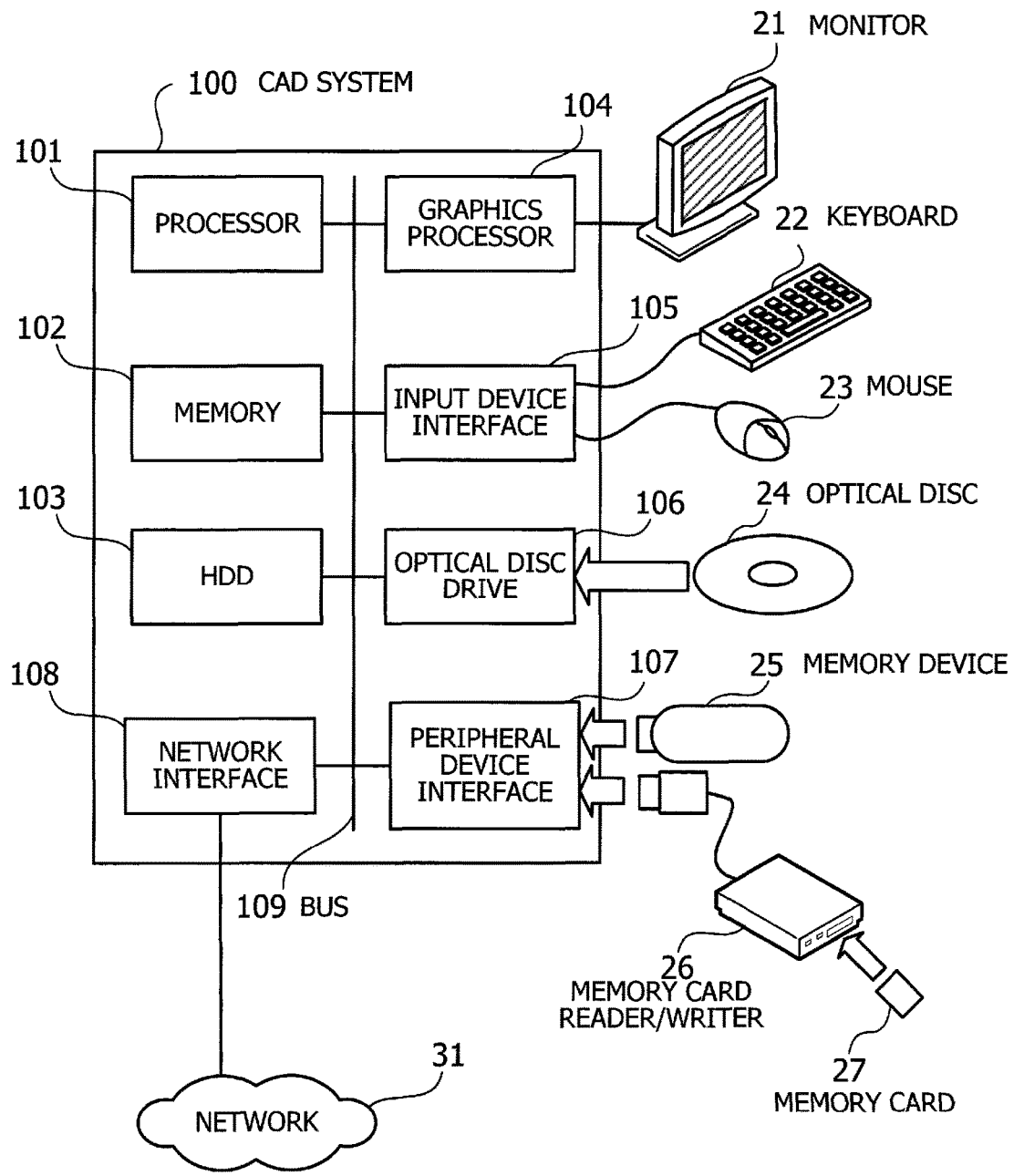
FIG. 3 illustrates an exemplary hardware configuration of a computer-aided design (CAD) system.

FIG. 3 illustrates an exemplary hardware configuration of a CAD system. The illustrated CAD system 100 includes a processor 101 to control its entire operation. The processor 101 is coupled to a memory 102 and other various devices and interfaces on a bus 109. The processor 101 may be a single processing device or a multiprocessor system including two or more processing devices, which may be, for example, a central processing unit (CPU), micro processing unit (MPU), or digital signal processor (DSP). It is also possible to implement the processing functions of the processor 101 wholly or partly in an application-specific integrated circuit (ASIC), programmable logic device (PLD), or other electronic circuits, or their combinations.

The memory 102 serves as a primary storage device of the CAD system 100. Specifically, the memory 102 is used to temporarily store at least some of the operating system (OS) programs and application programs that the processor 101 executes, in addition to other various data objects that it manipulates at runtime. The memory 102 may be, for example, random access memory (RAM) or other volatile semiconductor memory devices.

Other components on the bus 109 include a hard disk drive (HDD) 103, a graphics processor 104, an input device interface 105, an optical disc drive 106, a peripheral device interface 107, and a network interface 108.

The HDD 103 writes and reads data magnetically on its internal platters. The HDD 103 serves as a secondary storage device in the CAD system 100 to store program files and data files relating to the operating system and applications. Flash memory and other semiconductor memory devices may also be used as secondary storage devices, similarly to the HDD 103.

The graphics processor 104, coupled to a monitor 21, produces video images in accordance with drawing commands from the processor 101 and displays them on a screen of the monitor 21. The monitor 21 may be, for example, a cathode ray tube (CRT) display or a liquid crystal display.

The input device interface 105 is used to connect input devices such as a keyboard 22 and a mouse 23 and supply signals from these devices to the processor 101. The mouse 23 is a pointing device, which may be replaced with other kinds of pointing devices such as touchscreen, tablet, touchpad, and trackball.

The optical disc drive 106 reads out data encoded on an optical disc 24, by using laser light or the like. The optical disc 24 is a portable data storage medium, the data recorded on which can be read as a reflection of light or the lack of the same. The optical disc 24 may be a digital versatile disc (DVD), DVD-RAM, compact disc read-only memory (CD-ROM), CD-Recordable (CD-R), or CD-Rewritable (CD-RW), for example.

The peripheral device interface 107 is a communication interface for connecting some peripheral devices to the CAD system 100. For example, the peripheral device interface 107 may be used to connect a memory device 25 and a memory card reader/writer 26. The memory device 25 is a data storage medium with a capability of communicating with the peripheral device interface 107. The memory card reader/writer 26 is an adapter used to write data to or read data from a memory card 27, which is a data storage medium in the form of a small card. The network interface 108 is connected to a network 31 to exchange data with other computers or network devices (not illustrated).

Figure 4:
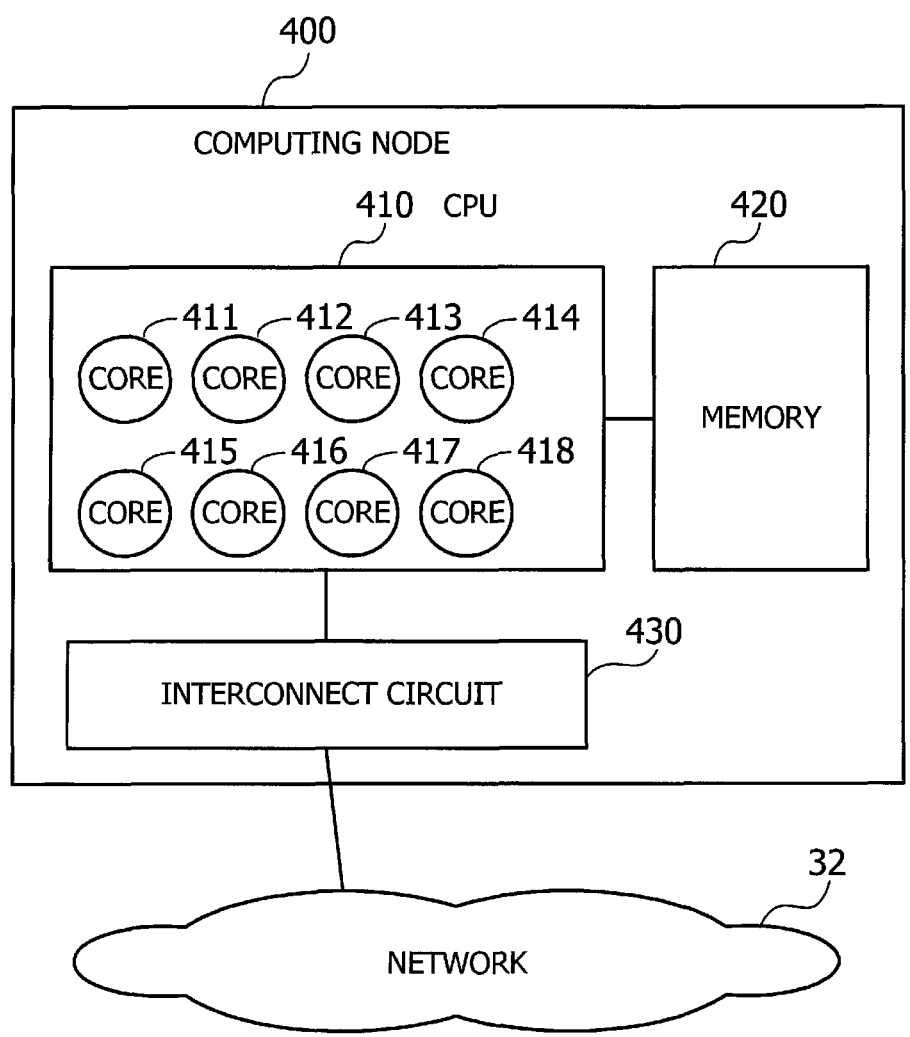
FIG. 4 illustrates an exemplary hardware configuration of a computing node.

FIG. 4 illustrates an exemplary hardware configuration of a computing node. The illustrated computing node 400 includes a CPU 410, a memory 420, and an interconnect circuit 430. The CPU 410 is a multi-core processor containing a plurality of processor cores 411 to 418 capable of executing multiple processes in parallel. The memory 420 stores programs that the CPU 410 executes, as well as various data that the CPU 410 manipulates during the course of to execution. For example, the memory 420 serves as a primary storage device to store programs for coronary circulation simulation. The interconnect circuit 430 is a communication circuit designed for high-speed optical communication. The computing node 400 uses this interconnect circuit 430 to exchange data with other computing nodes 400, 500, 600, . . . via a network 32. The interconnect circuit 430 is also used to read out and transfer cardiac model data from the storage device 300 to the CPU 410 via the network 32.

The above hardware configuration serves as a platform of processing functions to implement the second embodiment. It is noted that the foregoing vascular data generation apparatus 10 of the first embodiment may also be implemented on the hardware platform discussed in FIG. 3 for the CAD system 100 of the second embodiment.

The CAD system 100 provides various processing functions of the second embodiment by, for example, executing programs stored in a computer-readable medium. These processing functions of the CAD system 100 are encoded in the form of computer programs, which may be stored in a variety of media including HDDs. For example, the processor 101 loads the memory 102 with at least part of the programs stored in the HDD 103 and executes the programs on the memory 102. It is also possible to store the programs files in an optical disc 24, memory device 25, memory card 27, or the like. The programs stored in such a portable storage medium are installed in the HDD 103 under the control of the processor 101, so that they are ready to execute upon request. It may also be possible for the processor 101 to execute program codes read out of a portable storage medium, without installing them in its local storage devices.

Figure 5:
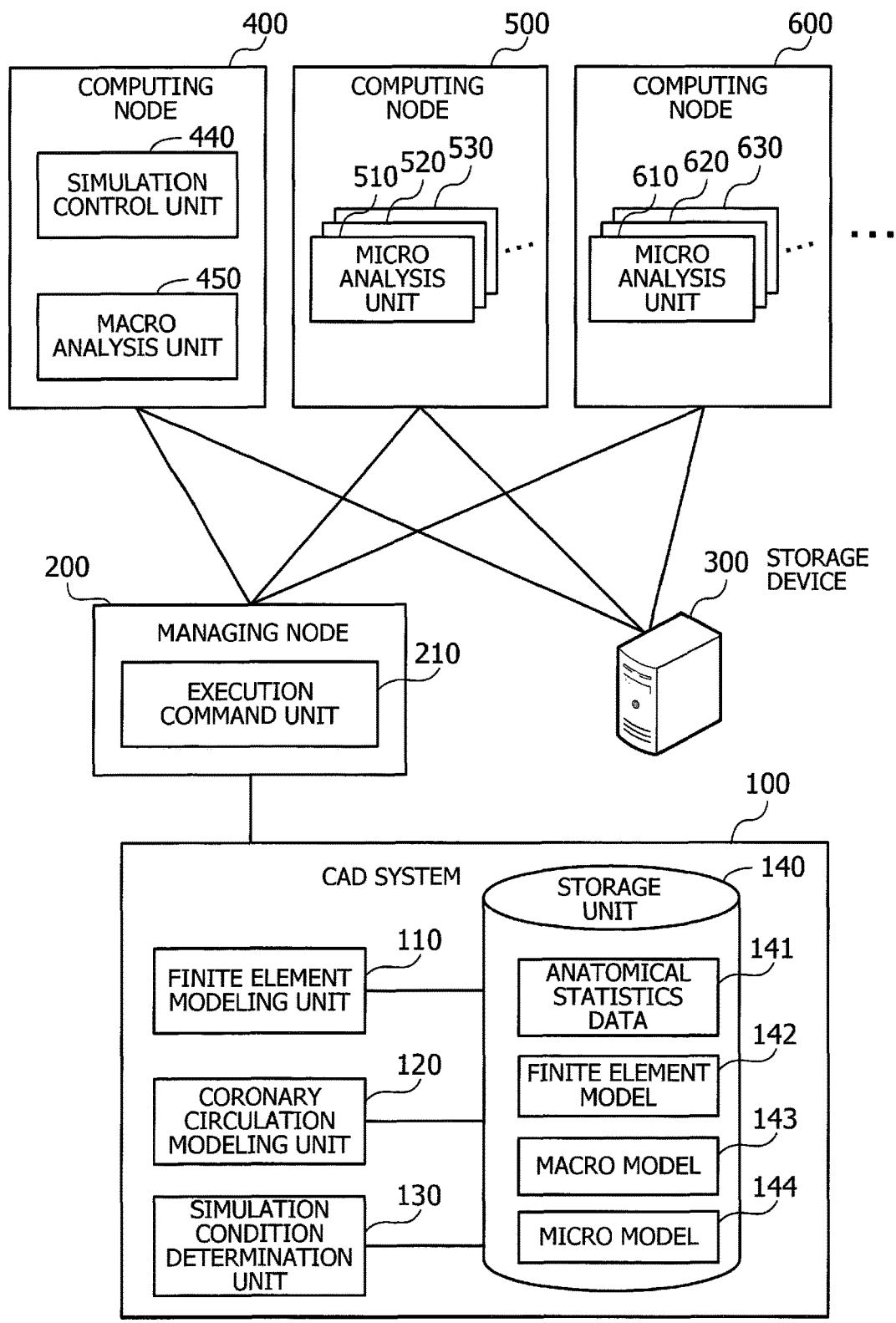
FIG. 5 is a functional block diagram of components that constitute the second embodiment.

According to the second embodiment, each constituent component of the proposed system provides functions described below. FIG. 5 is a functional block diagram of components that constitute the second embodiment. Seen in the lower half of FIG. 5 is a CAD system 100 including a finite element modeling unit 110, a coronary circulation modeling unit 120, a simulation condition determination unit 130, and a storage unit 140. The finite element modeling unit 110 produces a finite element model representing the solid geometry of a heart, according to commands from the user. This finite element model may be organized in the form of three-dimensional meshes of, for example, tetrahedrons. The tetrahedral meshes have been mentioned in the first embodiment as an example of polyhedron elements of a model. The coronary circulation modeling unit 120 produces a coronary circulation model according to commands from the user, which represents a vascular network of a heart. Also according to user command, the simulation condition determination unit 130 determines under what conditions the coronary circulation simulation is to be executed. The execution conditions include, for example, how many micro models to connect to each pressure node of the cardiac muscle. The storage unit 140 stores anatomical statistics data 141, a finite element model 142, a macro model 143, and a micro model 144. A coronary circulation model is formed by combining the macro model 143 and micro model 144.

Seen in the middle of FIG. 5 is a managing node 200 and its execution command unit 210. This execution command unit 210 is configured to command a plurality of computing nodes 400, 500, 600, . . . to execute a coronary circulation simulation with the finite element model and coronary circulation model produced by the CAD system 100. For example, the execution command unit 210 first receives these two models from the CAD system 100 and stores them in a storage device 300. The execution command unit 210 then selects computing nodes to submit jobs of the coronary circulation simulation. For example, the execution command unit 210 may select every computing node that has no jobs to execute at the moment. In the case where a specific degree of parallelism is designated previously for the coronary circulation simulation, the execution command unit 210 selects as many computing nodes as needed to achieve the designated parallelism. The selected computing nodes are then to receive a job assignment. The execution command unit 210 further singles out one computing node for macro analysis while assigning the remaining computing nodes for micro analysis. The execution command unit 210 submits a job to the former computing node (e.g., the first computing node 400 in FIG. 5) to perform a macro analysis, as well as to control the entire process of simulation. The execution command unit 210 also submits jobs to the remaining computing nodes (e.g., the second, third, and subsequent computing nodes 500, 600, . . . in FIG. 5) to perform a micro analysis.

As already mentioned, the storage device 300 is where a finite element model 142, macro model 143, and micro model 144 are stored in preparation for a coronary circulation simulation. The data in this storage device 300 is referenced by each computing node 400, 500, 600, . . . during the coronary circulation simulation The first computing node 400 includes a simulation control unit 440 and a macro analysis unit 450. The simulation control unit 440 controls the entire process of a coronary circulation simulation. The macro analysis unit 450 undertakes a macro-modeling part of the coronary circulation simulation, such as the analysis of heart beats produced by myocardial contraction and relaxation and the blood flows in large coronary arteries and veins. The simulation control unit 440 and macro analysis unit 450 are functions realized as part of macro analysis jobs that the managing node 200 submits to the first computing node 400.

The second computing node 500 includes a plurality of micro analysis units 510, 520, 530, . . . to analyze the blood flows in medium-scale vessels, arterioles venules, and capillaries. These micro analysis units 510, 520, 530, . . . are functions realized as micro analysis jobs that are submitted to the computing node 500 and executed by different processor cores in its CPU.

The third computing node 600 similarly includes a plurality of micro analysis units 610, 620, 630, . . . to analyze the blood flows in medium-scale vessels, arterioles venules, and capillaries. These micro analysis units 610, 620, 630, . . . are functions realized as micro analysis jobs that are submitted to the computing node 600 and executed by different processor cores in its CPU.

It is noted that the coronary circulation modeling unit 120 in FIG. 5 is an example of an element including the first generating unit 12, second generating unit 13, and modifying unit 14 discussed previously in FIG. 1 for the first embodiment. Also the storage unit 140 is an example of the storage unit 11 discussed in FIG. 1 for the first embodiment.

As mentioned above, the storage device 300 stores several kinds of data objects. The following description will explain them in detail.

Figure 6:
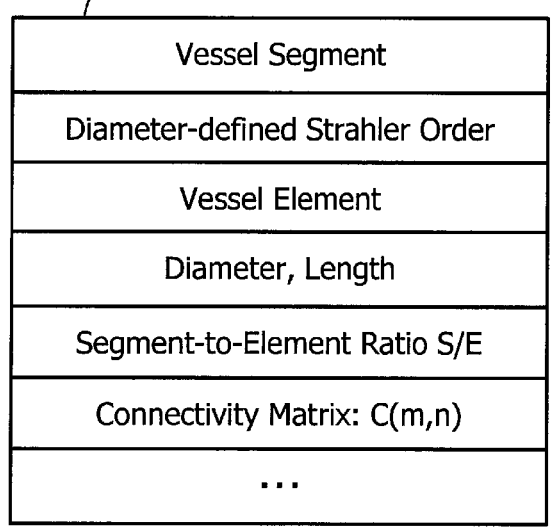
FIG. 6 illustrates an example of anatomical statistics data.

FIG. 6 illustrates an example of anatomical statistics data. As seen in FIG. 6, this anatomical statistics data 141 includes the following information items. Specifically, Vessel Segment refers to a part of a blood vessel that connects two bifurcation points. Each vessel segment has a particular diameter, length and order. It is assumed that the vessel diameter does not change within a segment.

Diameter-defined Strahler Order is a value assigned to each vessel segment for observation of diameter-dependent features (physical properties and the like) of vessels. This value derives from the concept of Strahler order used in the geomorphology and hydrology to determine the stream order of rivers. For example, vessel segments smaller than 8 µm in diameter are given an order number of zero as they are regarded as capillaries. Small vessel segments of coronary arteries merge into larger vessel segments toward the root (sinus of Valsalva) of their tree-structured network. Similarly, small vessel segments of coronary veins merge into larger vessel segments toward the root (right atrium, Thebesian sinus) of their tree-structured network. Let two integers n and m represent different orders of vessel segments. When two joining vessel segments have the same order n, the resulting vessel segment will be given an increased order of (n+1). When they have different orders n and m, the resulting vessel segment will be given an order of either n or m, whichever is larger. Every vessel segment is assigned a specific order number in this way, and then some adjustment is made to the orders such that their respective distributions of diameters will not overlap with each other. It is also noted that the sign of order numbers indicates whether the vessel segments are arteries or veins. For example, venous vessel segments have negative order numbers, while arterial vessel segments positive. According to an anatomical analysis of swine hearts, the order of their arteries ranges from 1 to 11, and that of their veins ranges from −1 to −12.

Vessel Element refers to a series of vessel segments with the same order. Diameter and Length are the average and standard deviation of vessel diameters and lengths of vessel segments and vessel elements of each order. Segment-to-Element Ratio S/E indicates the average and standard deviation of the number of vessel segments per element of each order.

Connectivity Matrix C(m, n) describes a branching structure of vessels. More particularly, the connectivity matrix represents in matrix form the average number of order-m elements that stem from one order-n element. For example, the average number of order-m elements is measured for each of the following six portions of the coronary circulation system: left anterior descending arteries and left circumflex arteries (both being left coronary arteries), right coronary arteries, veins into coronary sinus, and Thebesian veins. The measurement results of their numbers are analyzed and summarized as a connectivity matrix C(m, n).

FIG. 7 illustrates an exemplary data structure of a finite element model. The illustrated finite element model 142 is formed from a node data table 142a and a mesh data table 142b, where Nnodes represents the number of nodes, and Nmesh the number of meshes.

The node data table 142a indicates, in tabular form, the position of each node of a finite element model.

The nodes registered in this table serve as the vertices of tetrahedral meshes in the model. More specifically, the node data table 142a is formed from two data fields, one for node numbers and the other for their corresponding node coordinates. The node number field contains a unique identification number of a node. The node coordinate field contains x-, y-, and z-axis coordinate values of a node in a three-dimensional virtual space.

The mesh data table 142b defines the shape of each mesh in tabular form. More specifically, the mesh data table 142b is formed from two data fields, one for mesh numbers and the other for their corresponding sets of four node numbers representing a tetrahedral mesh. The mesh numbers are unique identification numbers indicating mesh.

FIG. 8 illustrates an exemplary data structure of a macro model. The macro model 143 represents a structure of large coronary arteries and veins as part of the cardiac vessel network. The illustrated macro model 143 includes a node data table 143a and a vessel segment data table 143b, where Nelem represents the number of vessel segments. The node data table 143a has the same structure as the foregoing node data table 142a in the finite element model 142 described above in FIG. 7.

The vessel segment data table 143b is, on the other hand, formed from the following data fields associated with each particular vessel segment: Segment Number, Node, Order, Diameter, and Conductance. The segment number field contains a unique identification number of a vessel segment. The node field contains unique identification numbers of two nodes located at the opposite ends of the vessel segment. The order field contains a value for classification of vessels based on their thickness. That is, the capillaries have the smallest order, and large vessels have larger order numbers. The diameter field indicates the diameter of the vessel segment.

FIG. 9 illustrates an exemplary data structure of a micro model representing intermediate vessel networks, arterioles, venules, and capillaries as part of a cardiac vessel network. The illustrated micro model 144 includes a node data table 144a and a vessel segment data table 144b, where Nelem represents the number of vessel segments. The node data table 144a has the same structure as the foregoing node data table 142a in the finite element model 142 described above in FIG. 7.

The vessel segment data table 143b is formed from the following data fields: Segment Number, Node, Order, Length, Diameter, Vessel Wall Elasticity, Reference Pressure Difference, and Quantity. The segment number field contains a segment number for identifying a specific vessel segment, and the node field contains identification numbers of two nodes located at the opposite ends of that vessel segment. The order field contains a value for classification of vessels based on their thickness. The length and diameter fields indicate the length and diameter of the vessel segment, respectively. The vessel wall elasticity field contains an elasticity coefficient of walls of the vessel segment. The reference pressure difference field gives a reference value of pressure difference between the blood pressure within a vessel and the inner pressure of the myocardium. This reference value is used together with the pressure difference at each simulation time point to calculate the diameter of vessels. The quantity field indicates how many segments are present in the same order, under the assumption of symmetry.

Figure 10:
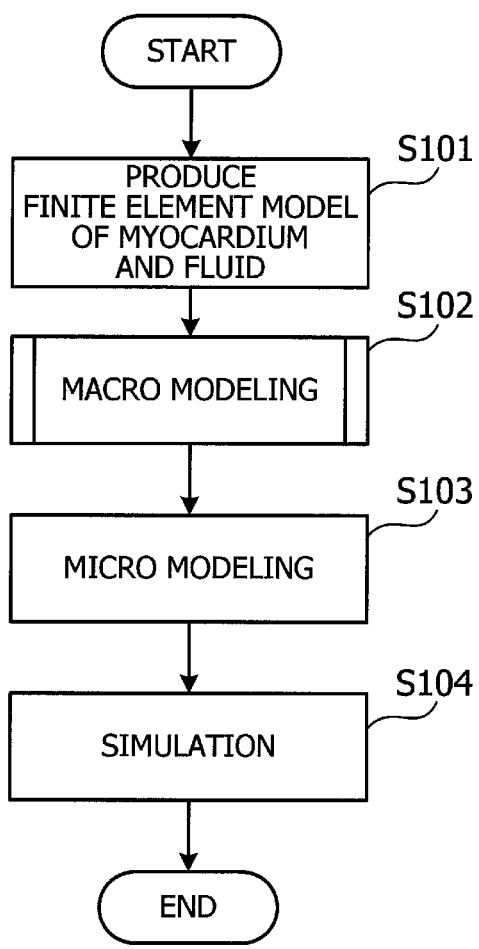
FIG. 10 is a flowchart illustrating an exemplary procedure of a coronary circulation simulation.

The components discussed in FIG. 5 work together to execute a coronary circulation simulation using various data discussed above in FIGS. 7 to 9. FIG. 10 is a flowchart illustrating an exemplary procedure of a coronary circulation simulation.

(Step S101) The user interacts with the CAD system 100 to initiate a simulation. The finite element modeling unit 110 in the CAD system 100 produces a finite element model 142 according to user inputs. The produced finite element model 142 is sent to the managing node 200, and the managing node 200 stores it in the storage device 300.

(Step S102) The coronary circulation modeling unit 120 in the CAD system 100 produces a macro model 143 according to user inputs. The CAD system 100 stores the produced macro model 143 in its local storage unit 140.

(Step S103) The coronary circulation modeling unit 120 produces a micro model 144 according to user inputs. The CAD system 100 stores the produced micro model 144 in its local storage unit 140.

(Step S104) The execution command unit 210 in the managing node 200 submits jobs to a plurality of computing nodes and requests them to execute a coronary circulation simulation. The computing nodes execute the simulation as requested, by using a plurality of processor cores in parallel.

Each of the above steps of FIG. 10 will now be described in detail below.

(a) Finite Element Modeling

The CAD system 100 receives medical image data of, for example, the computed tomography, magnetic resonance image, or echocardiogram. The finite element modeling unit 110 extracts geometric data of a heart from the received images and divides the data into meshes (e.g., tetrahedral or hexahedral meshes) suitable for the finite element method.

Figure 11:
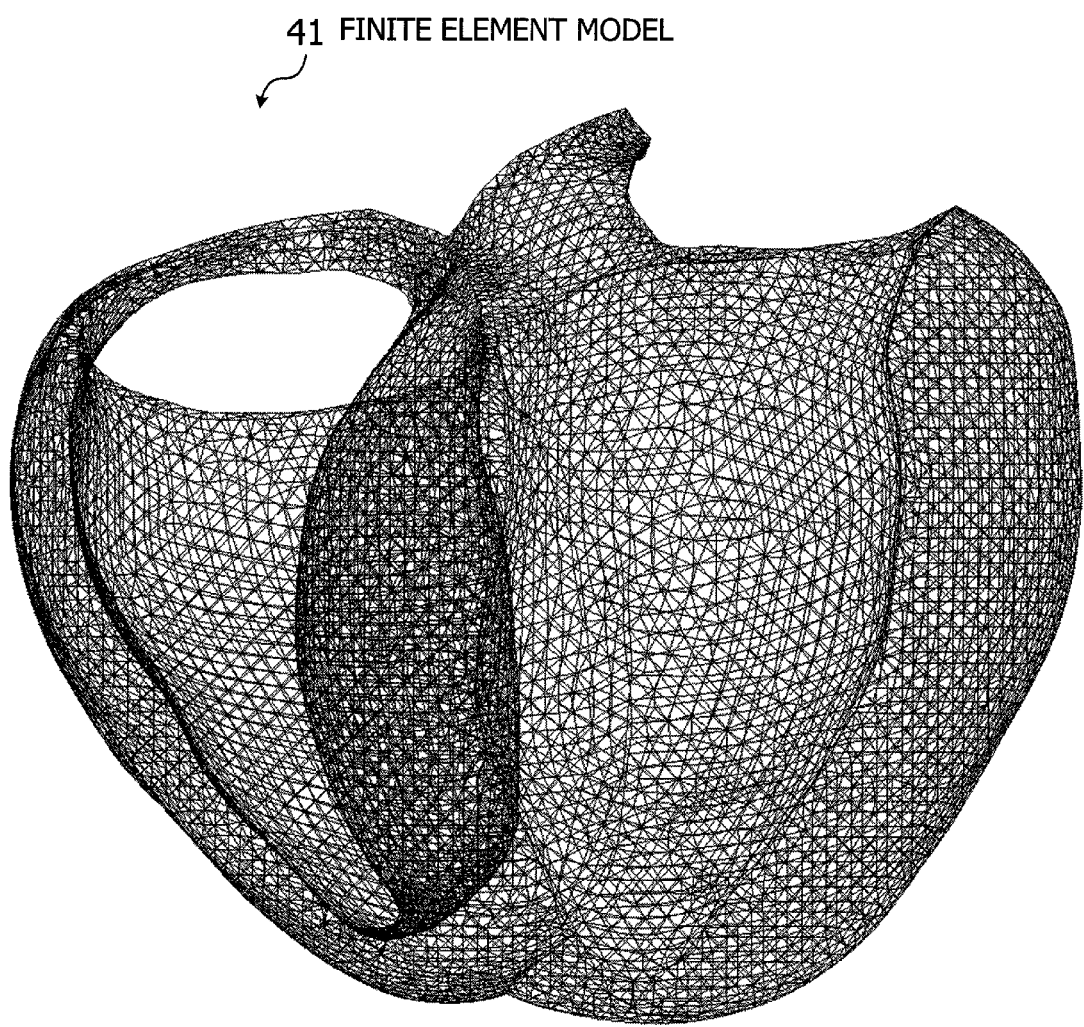
FIG. 11 illustrates an example of a finite element model.

FIG. 11 illustrates an example of a finite element model. This finite element model 41 has been produced by dividing a myocardium into a plurality of meshes. More specifically, a myocardium with a volume of 166.6 ml has been divided into 219,311 elements with 43,293 nodes.

(b) Macro Modeling of Coronary Circulation

The modeling process of coronary circulation is divided into two parts, macro modeling and micro modeling. Macro modeling uses a method based on anatomical statistics data in combination with a method based on optimal modeling.

Figure 12:
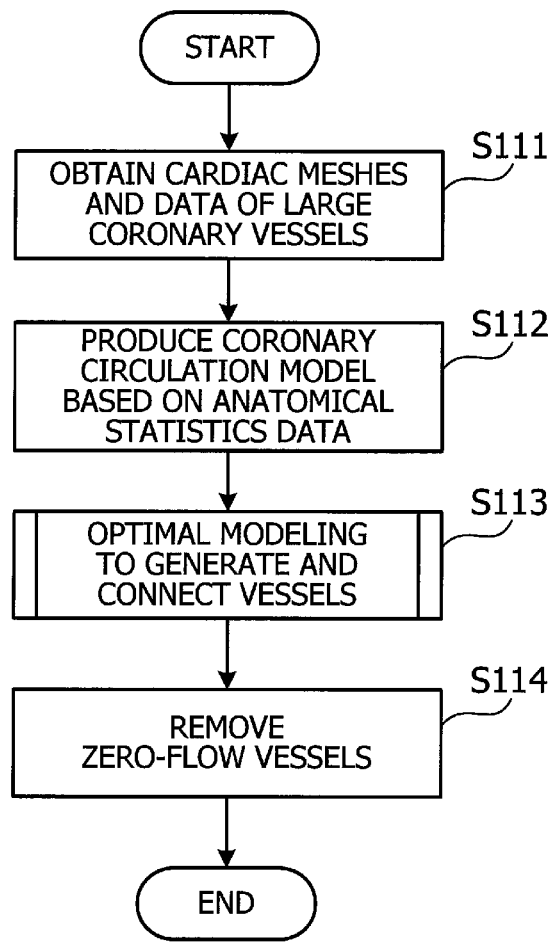
FIG. 12 is a flowchart illustrating an exemplary procedure of macro modeling.

FIG. 12 is a flowchart illustrating an exemplary procedure of macro modeling.

(Step S111) The coronary circulation modeling unit 120 obtains data of cardiac meshes and large coronary vessels. These things may have been entered by the user.

(Step S112) The coronary circulation modeling unit 120 performs modeling of coronary circulation by using a modeling method based on anatomical statistics data.

(Step S113) The coronary circulation modeling unit 120 then subjects the resulting coronary circulation model to a method based on optimal modeling to generate and connect blood vessels at end points of the existing network. This method produces an optimal model by, for example, placing vessels such that their end points will be placed at the nodes of myocardial meshes.

(Step S114) Upon completion of the vessel generation and connection based on the optimal modeling, the coronary circulation modeling unit 120 removes some of the vessel segments produced from anatomical statistics data when they are found to have no assigned flow rates (blood flows). For example, some vessel segments may be too long to fit the target condition of the optimization, i.e., minimizing the volume of vessels. The foregoing method based on optimal modeling does not add new vessels or assign blood flows to such long vessel segments. The coronary circulation modeling unit 120 removes these zero-flow vessels from the coronary circulation model.

Figure 13:
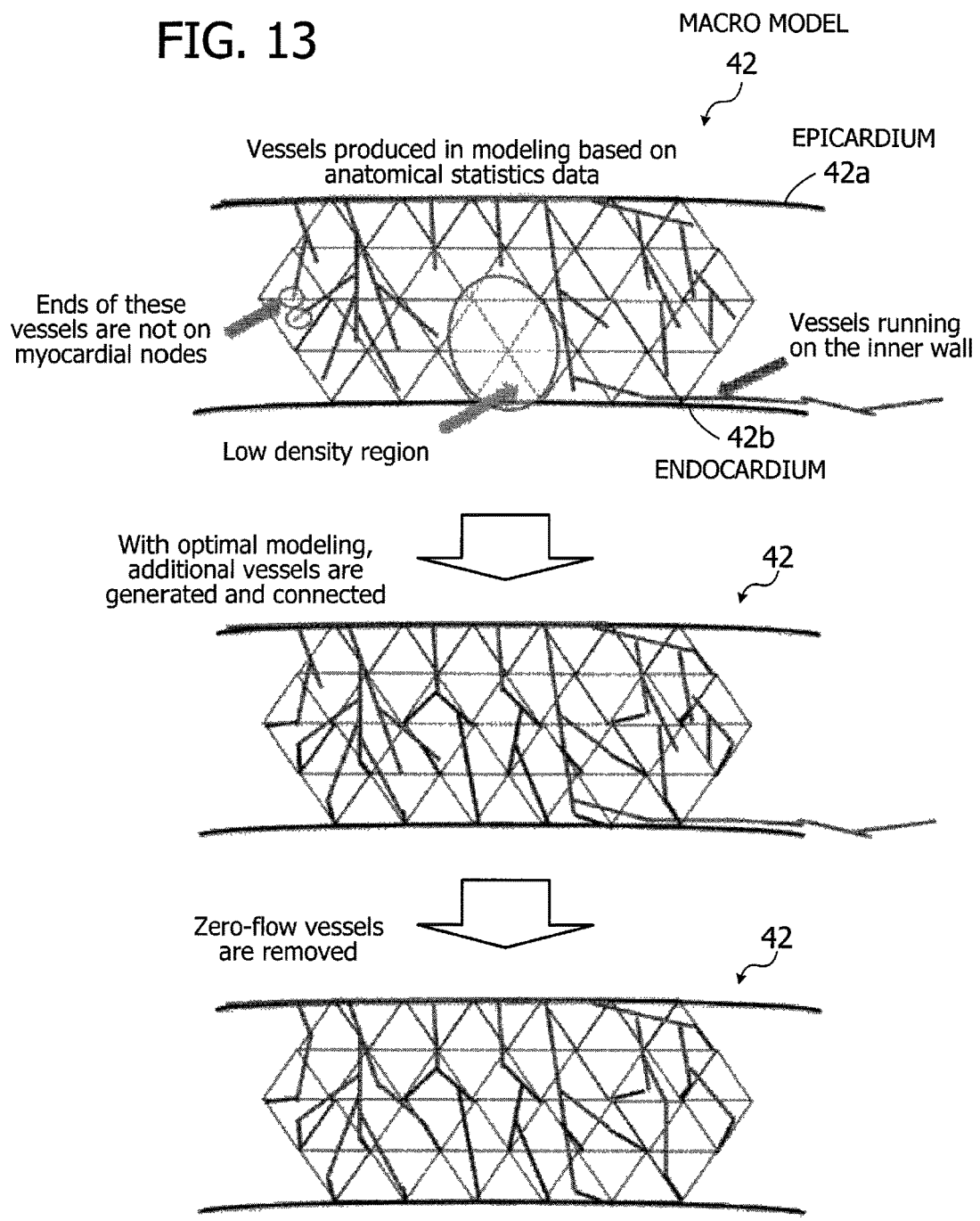
FIG. 13 explains a process of producing a macro model by way of example.

FIG. 13 explains a process of producing a macro model by way of example. FIG. 13 includes three illustrations of a macro model 42, in each of which the upper bold arc represents epicardium 42*a* (outermost layer of heart tissue), and the lower bold arc represents endocardium 42*b* (innermost layer of heart tissue). The triangles seen in the macro model 42 indicate finite element meshes used in the heart simulation.

First, an initial version of coronary circulation model (macro model 42) is produced with a method based on anatomical statistics data. In the macro model 42 at this stage, the end points of vessels do not lie on the myocardial nodes. The macro model 42 at this stage has the following problems:

(i) Some regions exhibit an extremely low density of vessels.

(ii) Some vessels run on the inner wall, which contradict to the observation.

To solve the above problems, the initial macro model 42 is subjected to a method based on optimal modeling. This method generates and connects additional vessels to some exiting vessels selected out of those in the initial macro model 42. For example, the method places one end of a new vessel at a node of the myocardial meshes and connects the other end with the extreme end of an existing vessel selected by the method. This is repeated for all nodes, thus producing additional vessels (blue in FIG. 13) connecting existing vessels (red in FIG. 13) in the macro model 42 with myocardial nodes. The middle diagram in FIG. 13 depicts such new vessels added to the myocardial nodes, while omitting some of them for the purpose of clarity. The noted method of optimized modeling offers the following advantages.

(i) Minimum volume modeling enables construction of a vascular network with more natural form of vessels. For example, minimum volume modeling would avoid placing a new vessel between a myocardial node and an end point of existing vessels if their distance is unrealistically long. This logic prevents the vessel volume of the model from being increased by unnatural vessels with inappropriate lengths.

(ii) It is possible to eliminate low-density regions in the initial model, which are unnatural from the anatomical viewpoint. The elimination is achieved by filling them with new vessels, with their end points placed at the nodes of uniformly-sized myocardial meshes.

(iii) It is possible to model the right coronary artery running along the boundary between the right ventricle and atrium, for example. Such vessels are difficult to reproduce in a model with the optimal modeling method alone.

As a result of the above vessel generation and connection based on optimal modeling, most vessels in the macro model 42 terminate at myocardial nodes. Some vessels, however, remain unconnected to the nodes.

In view of the above, the last step of the macro modeling process is to find vessels having no downstream vessel connections and prune them from the macro model 42. This removal of vessels eliminates unrealistic vessels such as those running on the inner wall. For example, the minimum volume modeling such as CCO tries to construct vessels in a form that delivers blood efficiently to the microcirculation system because that is the role of conduit vessels (arteries with a diameter of 100 µm or more). From this standpoint of minimum volume modeling, a consistently thick blood vessel creeping over the inner wall of the heart is considered to be inefficient and thus unsuitable for the role of blood-supplying conduits. Such vessels are deleted from the macro model since the CCO gives no vessel connections or blood flows to them.

The outline of macro modeling has been discussed above. The following subsections will provide more details of each step of the flowchart of FIG. 12.

b1) Obtain Cardiac Meshes and Data of Larger Coronary Vessels

Myocardial meshes are generated by the finite element modeling unit 110. Large coronary arteries or veins are obtained through the analysis of images supplied from a medical diagnostic imaging system (e.g., CT, MRI). The minimum diameter of vessels seen in these images is about one millimeter (which may actually depend on the performance of diagnostic devices).

Figure 14:
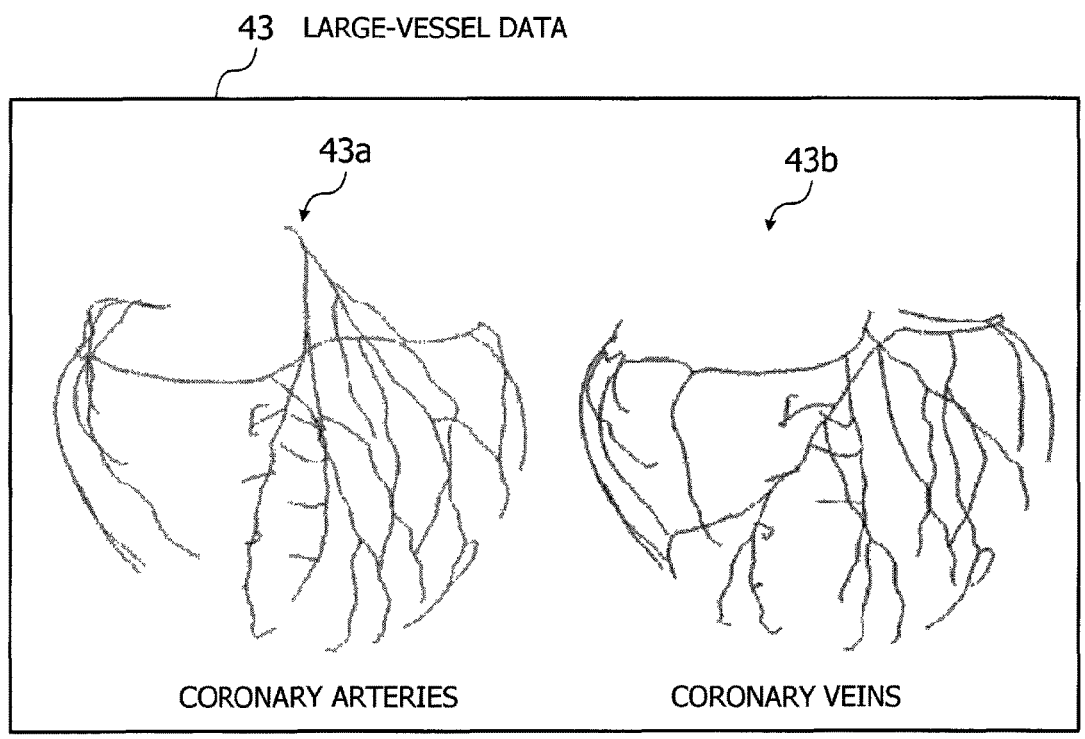
FIG. 14 illustrates an example of data representing large vessels.

FIG. 14 illustrates an example of data representing large vessels. The illustrated large-vessel data 43 includes data of coronary arteries 43*a* and coronary veins 43*b*. As discussed previously in FIG. 8, the vascular data of coronary circulation is formed from nodes representing spatial positions and vessel segments each representing a line segment that connects two nodes. The data of vessel segments includes parameters that give their diameters (or radiuses) and orders, for example.

The user enters such large-vessel data 43 to the CAD system 100 by, for example, specifying locations of coronary arteries and veins in cardiac images supplied from a medical diagnostic imaging system. The user also enters the thickness and order number of these coronary arteries or veins to the CAD system 100.

Inside the CAD system 100, the coronary circulation modeling unit 120 stores the entered values in a storage unit 140 as part of a macro model 143. For example, the coronary circulation modeling unit 120 populates the node data table 143*a* and vessel segment data table 143*b* of FIG. 8 with the entered values of large-vessel data 43. The coronary circulation modeling unit 120 may add, for example, a flag to the records of large-vessel data 43 to indicate that their origin is medical images. The coronary circulation modeling unit 120 may test this flag when modifying some parameters of vessel records in later processing. If the flag indicates that the records are derived from medical images, then the coronary circulation modeling unit 120 leaves the vessels unchanged as having constant parameters.

b2) Perform Modeling Based on Anatomical Statistics Data

This subsection describes a modeling method based on anatomical statistics data. The anatomical statistics data may be, for example, a set of detailed anatomical measurement data about coronary arteries, coronary veins, and capillaries of a swine heart in a diastolic state. This measurement data includes the diameter (or radius) and length of each vessel element between bifurcation points of vessels. Each vessel segment is given a specific order (e.g., diameter-defined Strahler order) depending on its diameter.

The anatomical statistics data 141 offers information described previously in FIG. 6, based on which the coronary circulation modeling unit 120 produces a coronary circulation model (macro model). For example, the coronary circulation modeling unit 120 first produces coronary circulation data with no spatial coordinates, using the large-vessel data, anatomical statistics data, and random numbers. The coronary circulation modeling unit 120 then maps the coronary circulation data on the finite element model of a heart such that the resulting vessels will run in the same way as in a real coronary circulation system. This mapping operation gives special coordinates to the vessels.

FIG. 15 illustrates an example of how a coronary circulation model (macro model) is produced. As can be seen from FIG. 15, what is prepared in the first place is coronary circulation data 44 having no spatial coordinate information associated with a heart. The coronary circulation data 44 is then mapped on a finite element model 41, and this mapping operation yields a macro model 45 of coronary circulation.

The following description will now provide details of how to produce coronary circulation data with no spatial coordinate information.

As discussed above, the anatomical statistics data includes the average and standard deviation of diameters, as well as lengths, of elements on each order. These parameters represent a normal distribution of vessel dimensions, and the coronary circulation modeling unit 120 uses them in combination with random numbers to determine a diameter and length of vessel segments or elements of each specified order. The determined dimensions thus adhere to the given statistics data of vessels.

The coronary circulation data is produced by repeating the following three procedural stages:

(i) First Stage: The coronary circulation modeling unit 120 determines order m of vessels branching from a node of an order-n vessel segment specified in the large-vessel data (input) by using the connectivity matrix C(m, n) and random numbers generated. The coronary circulation modeling unit 120 then converts some relevant values in the connectivity matrix into generation rates of each order by normalizing the average number of order-m vessels generated from an order-n element, where m ranges from 1 to 11 for arteries and from −1 to −12 for veins. With the obtained generation rate of each order, the coronary circulation modeling unit 120 determines the order of a branching vessel element.

(ii) Second Stage: The Vessel Element whose order has been determined above is supposed to include a certain number of vessel segments. The coronary circulation modeling unit 120 determines this number of vessel segments by using a random number to choose a value from the normal distribution of Segment-to-Element Ratios, which is specified as their average and standard deviation.

(iii) Third Stage: The coronary circulation modeling unit 120 determines the diameter and length of vessel segments according to their respective normal distributions similarly to the second stage described above. The determined diameter of vessel segments also indicates the diameter of the element that they constitute.

The coronary circulation modeling unit 120 repeats the above first to third procedural stages to produce vessel segments branching from each element until the first stage produces a vessel that is thinner than order 6 or order −6. When every element stops generating branches, the coronary circulation modeling unit 120 exits from the process of producing coronary circulation data.

The description will now provide details of mapping of coronary circulation data. According to the second embodiment, the node position x of a vessel segment is determined by solving an energy minimization problem. Here the energy f(x) is defined as follows:

$$f(x) = f1(x) + f2(x) + f3(x) \qquad (1)$$

The first function f1(x) on the right side denotes the energy for avoiding spatial overlap of the vessel segment in question with existing vessels that have already been placed. This energy f1(x) is inversely proportional to the vessel segment's distances from the midpoints of its surrounding vessels, and proportional to their capacities. The second function f2(x) represents the cost for enclosing x within the myocardium. This cost f2(x) increases as x comes close to the boundaries of epicardium, endocardium, or base of the heart. The third function f3(x) means the energy for bringing the bifurcation angle of vessels that is determined at position x nearer to an optimal bifurcation angle that minimizes the wall shearing stress. This energy f3(x) increases as the bifurcation angle deviates more from the optimal bifurcation angle.

The coronary circulation data includes multiple groups of vessel segments that are classified by their order numbers. The coronary circulation modeling unit 120 selects these groups in descending order of the absolute values of order numbers and further selects a pending node (i.e., node whose position is not determined yet) included in vessel segments of the selected group. The coronary circulation modeling unit 120 then uses equation (1) to determine the minimum-energy position for the selected node.

The coronary circulation modeling unit 120 now registers the vessel segments as a macro model 143 in the storage unit 140. More specifically, the node data table 143a and vessel segment data table 143b are populated with additional data that represents vessel segments produced by the modeling based on anatomical statistics data.

b3) Optimal Modeling to Generate and Connect Vessels

Coronary circulation data (macro model) has been produced above with a modeling method based on anatomical statistics data. This macro model is now subjected to a method based on optimal modeling to produce and connect additional vessels on the nodes of cardiac meshes. The second embodiment uses a minimum volume model as an example of optimal models.

Figure 16:
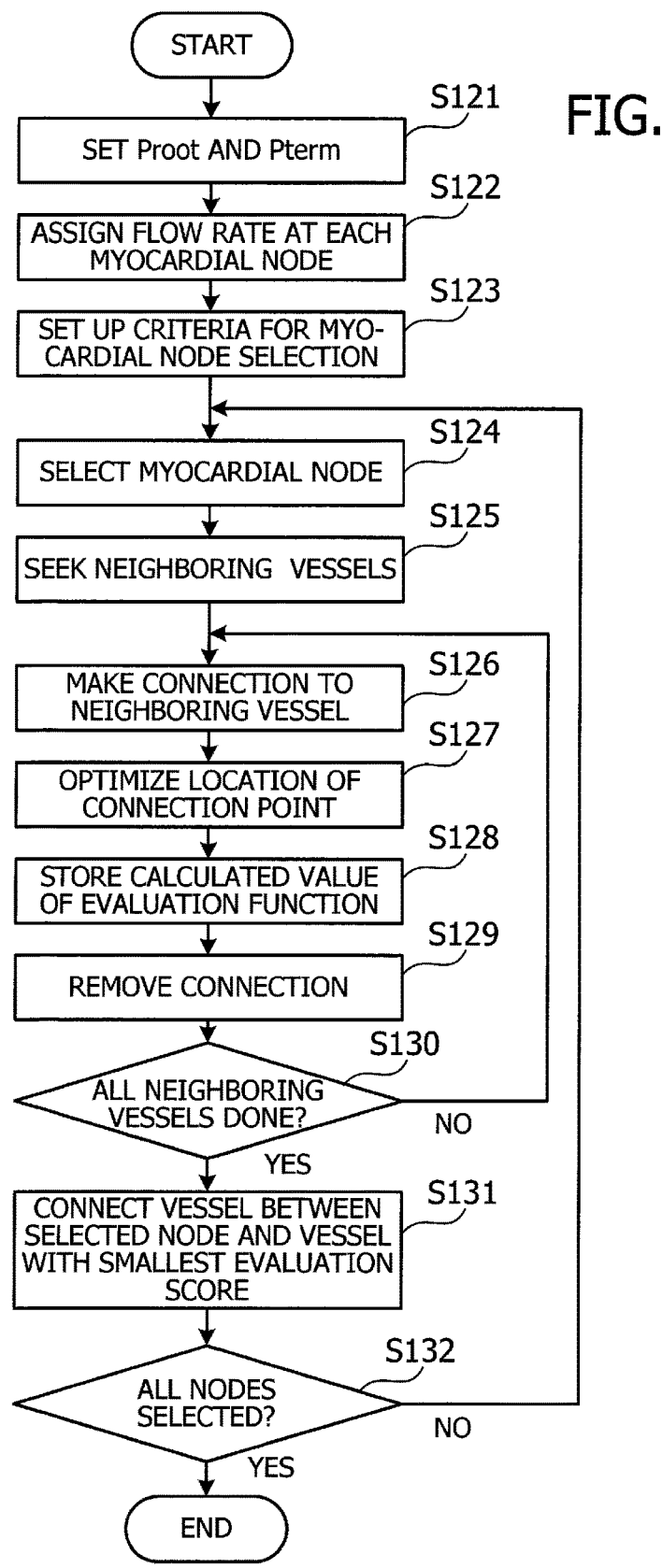
FIG. 16 is a flowchart illustrating an exemplary procedure of generating and interconnecting vessels based on optimal modeling.

FIG. 16 is a flowchart illustrating an exemplary procedure of generating and interconnecting vessels based on optimal modeling.

(Step S121) The coronary circulation modeling unit 120 sets up pressure conditions. For example, the coronary circulation modeling unit 120 specifies a pressure value $P_{root}$ at the topmost point (root) of the vascular network and another pressure value $P_{term}$ at the terminal points of vessels. $P_{root}$ in the coronary arteries represents the blood pressure in the sinus of Valsalva, in which the right and left coronary arteries originate.

(Step S122) The coronary circulation modeling unit 120 assigns flow rates at individual myocardial nodes. For example, the coronary circulation modeling unit 120 assigns higher flow rates to endocardial nodes than to epicardial nodes.

(Step S123) The coronary circulation modeling unit 120 sets up criteria for successive selection of myocardial nodes. For example, the coronary circulation modeling unit 120 determines selection criteria such that the successive selection will begin at a near-surface region of myocardium.

(Step S124) According to the selection criteria set up at step S123, the coronary circulation modeling unit 120 selects a pending myocardial node.

(Step S125) The coronary circulation modeling unit 120 seeks neighboring vessels around the selected node. For example, the coronary circulation modeling unit 120 extracts vessel segments in the vicinity of the currently selected myocardial node. These vessel segments are possible destinations of a new vessel segment to be produced and connected, and hence referred to also as "candidate vessels." For example, the distance between the selected node and the midpoint of each neighboring vessel segment is calculated, and the coronary circulation modeling unit 120 selects a predetermined number (e.g., 20) of vessel segments in ascending order their distances from the selected myocardial node.

(Step S126) The coronary circulation modeling unit 120 selects a neighboring vessel (candidate vessel) for evaluation and tentatively produces a vessel segment that extends from the selected myocardial node to that neighboring vessel.

(Step S127) The coronary circulation modeling unit 120 optimizes the connection point at which the vessel segment produced above connects to the selected neighboring vessel. This optimization uses a predetermined evaluation function that gives a specific energy value depending on the connection point of the vessel segment. The coronary circulation modeling unit 120 calculates an optimal position at which the energy becomes minimum and moves the connection point of the vessel segment to the optimal position. As an example of an optimal model for this energy calculation, the coronary circulation modeling unit 120 may evaluate the total volume of vessels, in which case a vascular network is produced to minimize the energy E that is defined as:

$$E = V \qquad (2)$$

where V represents the total volume of vessel segments.

(Step S128) The coronary circulation modeling unit 120 stores the calculated value of the evaluation function (referred to as the evaluation score) in a memory 102.

(Step S129) The coronary circulation modeling unit 120 removes the tentative connection from the selected myocardial node. For example, the coronary circulation modeling unit 120 deletes the vessel produced at step S126.

(Step S130) The coronary circulation modeling unit 120 determines whether all the neighboring vessels have been evaluated. When there remains any pending vessel, the process goes back to step S126. When all have been done, the process advances to step S131.

(Step S131) The coronary circulation modeling unit 120 finds a neighboring vessel with the smallest evaluation score and places a vessel again to connect the selected myocardial node with the found neighboring vessel, as well as optimizing its connection point so as to obtain an optimal evaluation score.

(Step S132) The coronary circulation modeling unit 120 determines whether all the myocardial nodes have been selected in the above steps. When all the myocardial node are done, the coronary circulation modeling unit 120 terminates the process. When there remains any pending myocardial node, the process goes back to step S124.

The above-described process permits the coronary circulation modeling unit 120 to add new vessel segments with their end points located at myocardial nodes.

Figure 17:
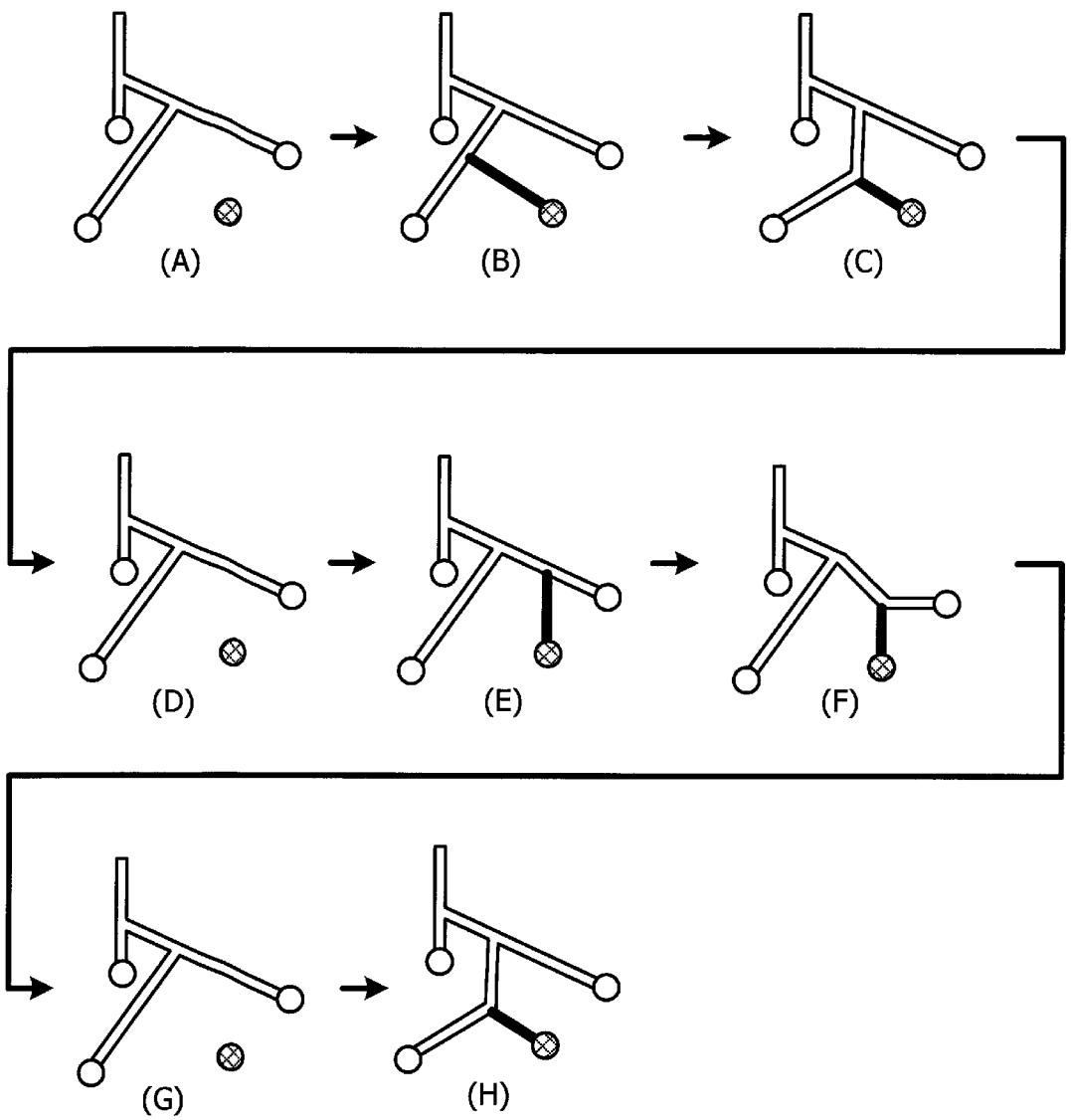
FIG. 17 illustrates an example of vessel connections made to neighboring vessels.

FIG. 17 illustrates an example of vessel connections made to neighboring vessels. As described above, the second embodiment attempts to make a vessel connection from a selected myocardial node to its neighboring vessels, one at a time, while calculating energy for each particular connection being attempted. The second embodiment finally chooses one neighboring vessel that exhibits the smallest energy and connects a vessel to that neighboring vessel. FIG. 17 illustrates how this connection process is executed.

The hatched circle seen in state (A) of FIG. 17 represents a myocardial node that is currently selected. State (B) illustrates a produced vessel (solid line) extending from the selected myocardial node to one of the existing vessels surrounding the node. For example, the produced vessel is connected at the midpoint of that neighboring vessel. This connection results in splitting the neighboring vessel into two vessel segments. In state (C), the connection node is moved to a minimum-energy point, and the energy value at that point is recorded. The connection is then removed in state (D), where the vessel network has reverted to its original state (A).

Then in state (E), another vessel is produced between the same selected myocardial node and a different neighboring vessel. In state (F), the connection node is moved to a minimum-energy point, and the energy value is recorded as done in State (C). The connection is removed in state (G), and the vessel network reverts again to its original state (A).

Lastly the energy values recorded in state (C) and state (F) are compared with each other, and a vessel connection is made in state (H) between the selected myocardial node and the neighboring vessel that exhibits a smaller energy value. The minimum-energy point of state (C) is adopted for the connection of this new vessel. As a result of the procedure seen in (A) to (H) of FIG. 17, the existing network has gained another vessel reaching a myocardial node.

The above procedure includes calculation of energy in a minimum volume model. As will be described below, this calculation actually includes update of parameters such as the radius of vessels.

Figure 18:
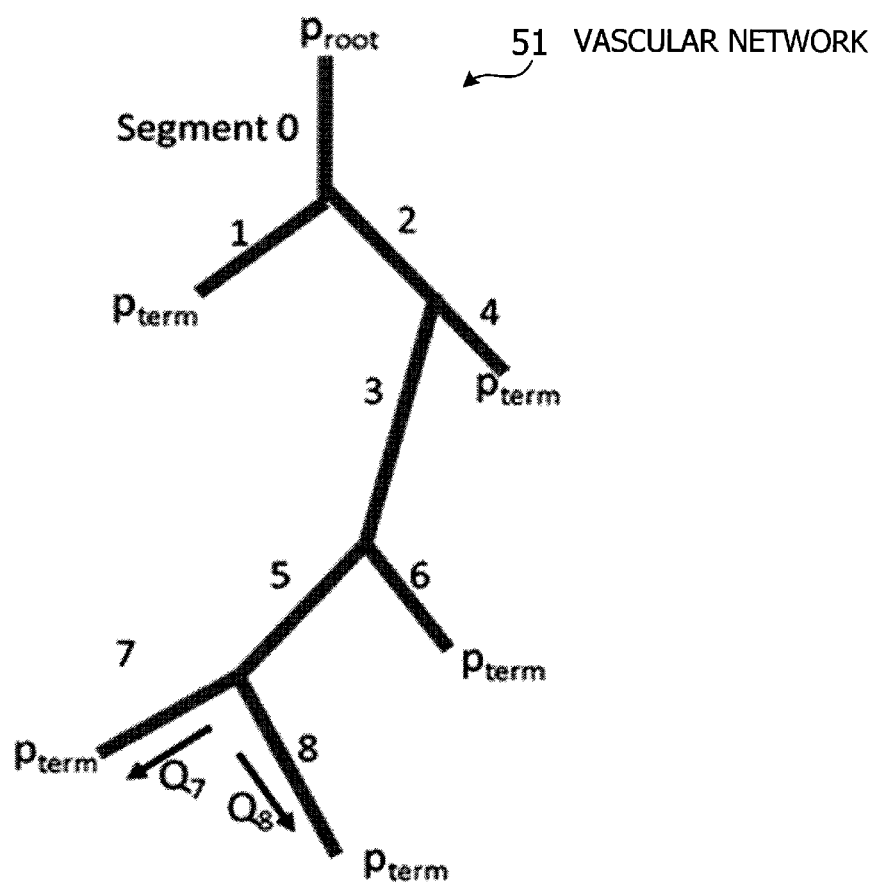
FIG. 18 exemplifies a vascular network subjected to energy calculation.

FIG. 18 exemplifies a vascular network subjected to energy calculation. When adding a new vessel segment to the illustrated vascular network 51, the coronary circulation modeling unit 120 calculates its energy by using parameters updated as follows. The illustrated vascular network 51 is made up of nine existing vessel segments, which are increasingly numbered from zero in the direction from their root (entrance of blood) toward the terminal ends. The following description refers to the i-th vessel segment as Segment i, where i is an integer equal to or greater than zero.

Segment i is a vessel located between two bifurcation points of the network in FIG. 18 and characterized by the following parameters:

Radius $r_i$

Length $l_i$

Blood flow $Q_i$ (within Segment i)

Resistance $R_i$ in terms of Hagen-Poiseuille flow

Combined resistance $R_{sub,i}$ of a subtree including Segment i as its root

More specifically, resistance $R_i$ is expressed as follows.

$$R_i = \frac{8\mu l_i}{\pi r_i^4} \qquad (3)$$

where parameter μ represents a kinematic viscosity of blood. The following formula defines a bifurcation ratio β indicating the ratio of radius between Segment i and vessels j branching off from Segment i.

$$\beta_i^j = \frac{r_j}{r_i} \quad (4)$$

It is also assumed here that the radius $r_{parent}$ of a vessel segment has the following relationship with the radiuses $r_{child0}$ and $r_{child1}$ of bifurcated vessel segments:

$$r_{parent}^\gamma = r_{child0}^\gamma + r_{child1}^\gamma \quad (5)$$

where parameter γ is a constant (e.g., γ=3) obtained through measurement experiments. $P_{root}$ and $P_{term}$ represent the pressures at the root and terminal points of the vascular network, respectively.

The calculation of parameters begins at the downstream ends and proceeds in the upstream direction. Bifurcation ratios $\beta_5^7$ and $\beta_5^8$ are now calculated as follows. First, the ratio of flow rate $Q_8$ of Segment 8 to flow rate $Q_7$ of Segment 7 is expressed as $$\frac{Q_8}{Q_7} = \frac{r_8^4}{l_8} \frac{l_7}{r_7^4} \quad (6)$$

This equation is transformed into $$\frac{r_8}{r_7} = \left(\frac{Q_8 l_8}{Q_7 l_7}\right)^{\frac{1}{4}} \quad (7)$$

Bifurcation ratios $\beta_5^7$ and $\beta_5^8$ are then obtained by the following two formulas.

$$\beta_5^7 = \frac{r_7}{r_5} = \left\{1 + \left(\frac{r_8}{r_7}\right)^\gamma\right\}^{-\frac{1}{\gamma}} = \left\{1 + \left(\frac{Q_8 l_8}{Q_7 l_7}\right)^{\frac{\gamma}{4}}\right\}^{-\frac{1}{\gamma}} \quad (8)$$

$$\beta_5^8 = \frac{r_8}{r_5} = \left\{1 + \left(\frac{r_8}{r_7}\right)^{-\gamma}\right\}^{-\frac{1}{\gamma}} = \left\{1 + \left(\frac{Q_8 l_8}{Q_7 l_7}\right)^{-\frac{\gamma}{4}}\right\}^{-\frac{1}{\gamma}} \quad (9)$$

Then the next bifurcation ratios $\beta_3^5$ and $\beta_3^6$ are calculated as follows. First, combined resistance $R_{sub,5}$ is expresses as $$R_{sub,5} = R_5 + \left(\frac{1}{R_7} + \frac{1}{R_8}\right)^{-1} = \frac{8\mu}{\pi r_5^4}\left[l_5 + \left\{\frac{(\beta_5^7)^4}{l_7} + \frac{(\beta_5^8)^4}{l_8}\right\}^{-1}\right] \quad (10)$$

The ratio of flow rate $Q_6$ of Segment 6 to flow rate $Q_5$ of Segment 5 is expressed as $$\frac{Q_6}{Q_5} = \frac{R_{sub,5}}{R_6} \quad (11)$$

This equation is transformed into $$\frac{r_6}{r_5} = \left(\frac{Q_6 l_6}{Q_5 l_5}\left[l_5 + \left\{\frac{(\beta_5^7)^4}{l_7} + \frac{(\beta_5^8)^4}{l_8}\right\}^{-1}\right]\right)^{\frac{1}{4}} \quad (12)$$

Bifurcation ratios $\beta_3^5$ and $\beta_3^6$ can then be obtained from the relationship of $r_3^\gamma = r_5^\gamma + r_6^\gamma$ as in equation (5). The calculation of $\beta_i^j$ is repeated similarly in the upstream direction, and the following result is obtained at last.

$$R_{sub,0} = R_0 + \left(\frac{1}{R_1} + \frac{1}{R_{sub,2}}\right)^{-1} = \frac{8\mu}{\pi r_0^4}\left[l_0 + \left\{\frac{(\beta_0^1)^4}{l_1} + \frac{(\beta_0^2)^4}{l_2}\right\}^{-1}\right] \quad (13)$$

Combined resistance $R_{sub,0}$ means the resistance of the vessel network as a whole, and the following equation holds.

$$P_{root} - P_{term} = R_{sub,0} Q_0 \quad (14)$$

Root radius $r_0$ is calculated from a given blood flow rate $Q_0$ at the root of the vessel network. Bifurcation ratios $\beta_i^j$ have all been determined during the course of the above calculation process. Accordingly the radius of every vessel segment is calculated based on the root radius $r_0$ and bifurcation ratios $\beta_i^j$, from upstream segments to downstream segments.

The above-described process has determined parameters of the existing blood vessels. The next description explains what calculation is performed when a new vessel segment is added.

Figure 19:
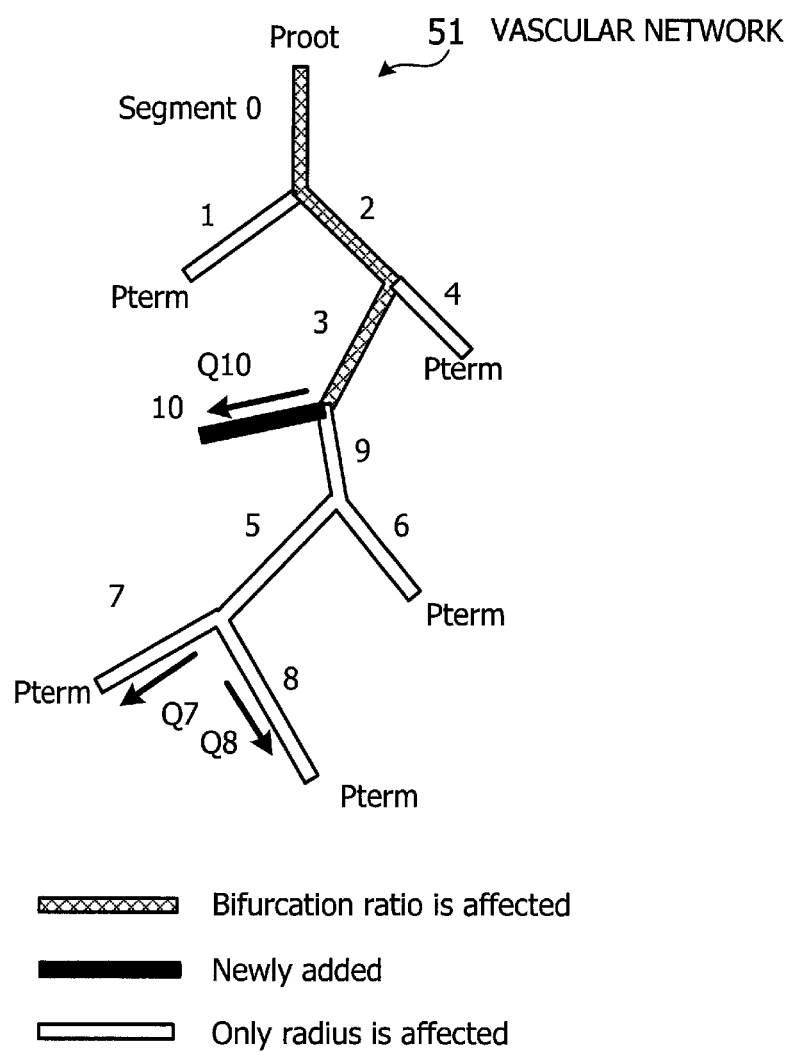
FIG. 19 illustrates what range of vessel parameters are changed upon addition of a new vessel segment.

FIG. 19 illustrates what range of vessel parameters are changed upon addition of a new vessel segment. Specifically, FIG. 19 assumes that the vascular network 51 of FIG. 19 has gained new Segment 10. The parameters are changed basically in the same way as discussed above in FIG. 18. Specifically, bifurcation ratios $\beta_i^j$ are re-calculated at only three vessel segments, Segment 0, 2, and 3. This is because the bifurcation ratios $\beta_i^j$ depend on the flow rates and lengths of vessel segments located downstream with respect to Segment i, as can be seen from, for example, equation (9). That is, optimization of the connection point between the new segment and existing segment affects the lengths of Segments 9 and 10 while holding their flow rates. A change of the bifurcation ratio thus occurs only at Segments 0, 2, and 3. The radius, on the other hand, varies at every vessel segment since the root radius $r_0$ changes.

Another example of energy calculation will now be described below. The previous example calculates vessel volume V as the energy E to be minimized. Alternatively, the following formula of energy is defined in order to build a more precise vascular network.

$$E = V + E_{med} + E_{shrink} \quad (15)$$

V is the total volume of vessels. $E_{med}$ is energy for preserving vessel segments whose diameters and lengths have been given as measurement data, typically obtained from medical images. $E_{shrink}$ represents a penalty introduced to prevent the connection point of a produced vessel segment from overlapping with end points of existing vessel segments as a result of optimization. Each of the noted energy terms will be described below.

(i) Vessel Volume V

This term corresponds to the total volume of vessels similar to the one used in the foregoing minimum volume model. It is noted that it excludes vessel segments supplying no blood to their end points, as discussed in FIG. 13. In other words, the calculation of vessel volume is performed only on the vessel segments whose flow rates are greater than zero.

(ii) Energy for Preserving Measurement Values ($E_{med}$)

The second embodiment uses medical images as one source of vessel data, whereas conventional minimum volume models do not take into consideration the use of such vessel data. For example, the data of large vessels discussed in FIG. 14 has been obtained from a medical diagnostic imaging system such as CT or MRI.

According to the observations of vessels in medical images, it is actually possible that one vessel bifurcates into two vessels whose diameters are equal to or slightly larger than that of the originating vessel. This reality, however, would not be reflected in a coronary circulation model if equation (5) is simply applied to the calculation of diameters of bifurcating vessels.

It is noted here that coronary circulation models are produced in two different situations with different intentions. One is when establishing a standard coronary circulation model, and the other is when building a patient-specific coronary circulation model for simulation of the patient's heart. In the latter case, the patient-specific coronary circulation model is preferably to preserve the details of measurement data, such as the diameters and lengths of large vessel segments of coronary arteries, obtained from medical images. For this reason, the second embodiment is designed to preserve the diameters and lengths of vessel segments produced on the basis of measurement on medical images. The following description will explain a method of calculating an optimal model without changing measurement values of vessel segments whose origin is medical images.

Figure 20:
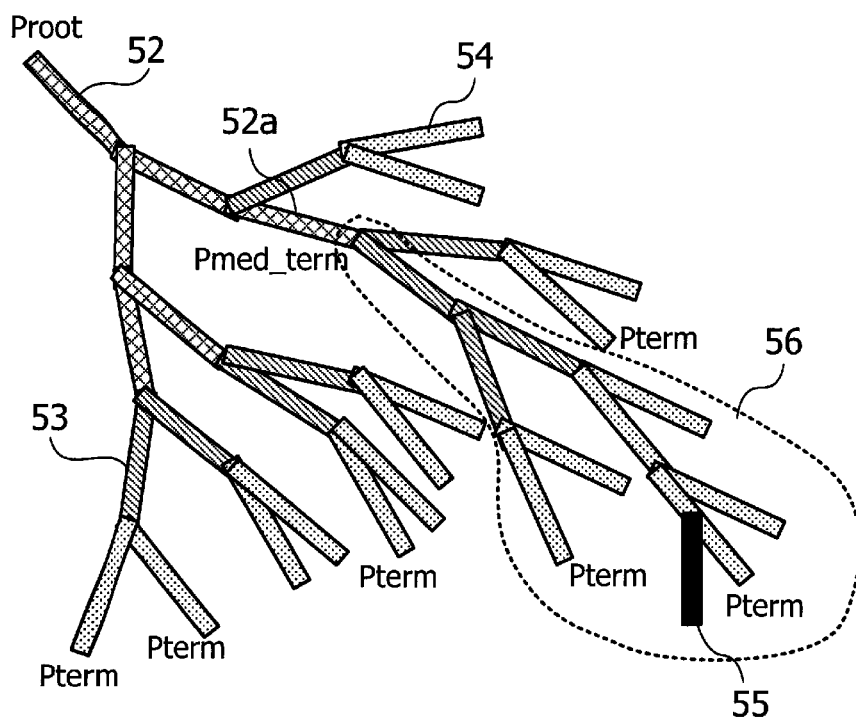
FIG. 20 illustrates an example of a vascular network in a coronary circulation model that includes vessel segments obtained from medical images.

FIG. 20 illustrates an example of a vascular network in a coronary circulation model that includes vessel segments obtained from medical images. The illustrated vascular network is made up of three groups of vessel segments. The topmost is a plurality of vessel segments 52 obtained from medical images. Connected to these vessel segments 52 are another plurality of vessel segments 53 produced with a method based on anatomical statistics data. Further connected to these vessel segments 53 are yet another plurality of vessel segments 54 produced with a method based on optimal modeling.

Suppose now that a new vessel segment 55 is to be added to the above vessel network. This vessel segment 55 will be one of the vessel segments produced with the optimal modeling-based method. Referring first to the vessel segments 52 obtained from medical images, their respective end-point pressures $P_{med\_term}$ are determined from the pressure $P_{root}$ and flow rate given at the root of the network because these vessel segments 52 have fixed diameters and lengths. Referring next to several vessel segments encircled by the broken line, these segments form a subtree 56 with a pressure of $P_{med\_term}$ at its upstream end. The foregoing algorithm of FIG. 16 may then be applied to this subtree 56.

As noted above, however, the pressure $P_{med\_term}$ is determined independently of end-point pressures $P_{term}$ of the subtree 56, and there may be a case of $P_{med\_term} < P_{term}$. This means the possibility of a reverse flow of blood. To avoid this contradiction (i.e., maintain the relationship of $P_{med\_term} > P_{term}$), the second embodiment introduces a penalty defined as follows.

$$E_{med} = \begin{cases} \dfrac{\alpha}{(P_{med\_term} - P_{term})^2}, & P_{med\_term} > P_{term} \\ \beta(P_{med\_term} - P_{term})^2, & P_{med\_term} \le P_{term} \end{cases} \quad (16)$$

This penalty includes two expressions to be applied depending on the specified conditions. The first one is a penalty applied when $P_{med\_term} > P_{term}$, which is expected not to allow these two values to become closer. The second one is a penalty applied when $P_{med\_term} \le P_{term}$, which is expected to correct the balance of pressures. Parameters $\alpha$ and $\beta$ are positive real numbers serving as their respective weighting coefficients.

The energy $E_{med}$ of equation (16) preserves the measurement values in the modeling process. That is, under the condition that upstream-end pressure $P_{med\_term}$ of the subtree 56 is greater than its end-point pressures $P_{term}$, energy $E_{med}$ becomes smaller as the difference between $P_{med\_term}$ and $P_{term}$ increases. Under the condition that upstream-end pressure $P_{med\_term}$ is smaller than or equal to end-point pressures $P_{term}$, energy $E_{med}$ becomes greater as the difference between $P_{med\_term}$ and $P_{term}$ increases. The optimization processing minimizes such energy values, thus making it possible to prevent the pressure at an upstream point from becoming lower than the pressure at downstream points while preserving the patient-specific parameters such as the measured thickness of vessels.

(iii) Penalty of Shrinkage ($E_{shrink}$)

The term "shrinkage" refers to a possible result of the connection node optimization for a new vessel segment; that is, the connection node of the new vessel segment may coincide with an existing end point of another vessel segment that shares the connection node. The noted end point is where the vascular network bifurcates, and the occurrence of shrinkage means producing an unnatural form of vessels by adding another vessel to an existing bifurcation point of the network.

Figure 21:
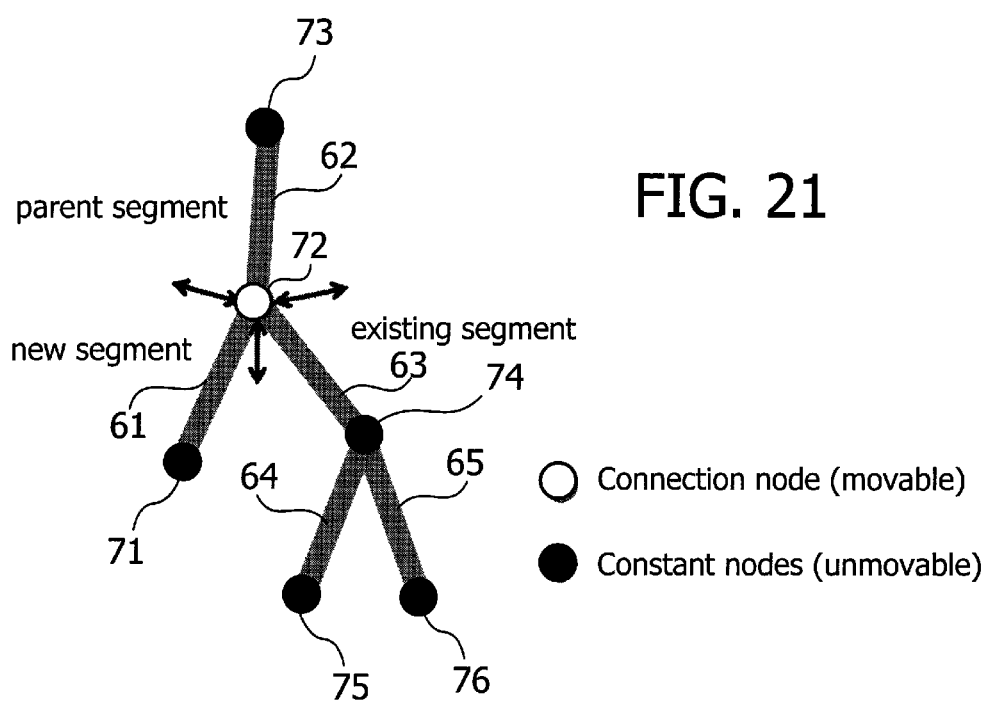
FIG. 21 illustrates an example of movements of a connection node to which a new vessel segment is added.

FIG. 21 illustrates an example of movements of a connection node (connection point) to which a new vessel segment is added. A new vessel segment 61 is connected to a connection node 72 on its parent vessel segment 62 and extends up to a myocardial node 71. The other end of the parent vessel segment 62 is at a node 73. The connection node 72 is shared by the new vessel segment 61 and an existing vessel segment 63. The latter vessel segment 63 bifurcate into vessel segments 64 and 65 at a node 74. The end points of these vessel segments 64 and 65 are connected to nodes 75 and 76, respectively. It is noted that the connection node 72 may be moved during the course of addition of the new vessel segment 61, whereas the other nodes are fixed.

Suppose now that the new vessel segment 61 has a length of $l_{new}$ and a radius of $r_{new}$, the parent vessel segment 62 has a length of $l_{parent}$ and a radius of $r_{parent}$, and the existing vessel segment 63 sharing the connection node 72 has a length of $l_{old}$ and a radius of $r_{old}$. To avoid occurrence of shrinkage, the second embodiment defines a penalty $E_{shrink}$ of vessel segment shrinkage as follows.

$$E_{shrink} = f_{shrink}(r_{new}, l_{new}) + f_{shrink}(r_{parent}, l_{parent}) + f_{shrink}(r_{old}, l_{old}) \quad (17)$$

where $$f_{shrink}(r, l) = \begin{cases} 0, & 2r \le l \\ \eta(2r - l)^2, & 2r > l \end{cases}$$

where parameter $\eta$ is a positive real number. According to this formula (17), the energy increases as there is a greater difference between the diameter (2r) and length (l) of a vessel segment when $2r > l$. This nature of $E_{shrink}$ applies to each of the vessel segments 61 to 63 sharing the connection node 72. Since large values of energy mean that the connection node 72 is not optimal, it is unlikely for the optimization algorithm to choose such locations for the connection node 72. In other words, the optimization algorithm is expected to avoid a choice of the connection node location that would render the lengths of vessel segments 61 to 63 shorter than their diameters. The use of this penalty $E_{shrink}$ of vessel segment shrinkage thus makes it possible to keep the connection node of a new vessel segment away from existing nodes of other vessel segments that share the connection node with the new segment.

Vessel segments are produced and connected to myocardial nodes in accordance with the algorithm of minimum volume modeling. This process includes various calculations using various constant parameters and variable parameters. The following is an example of values used in those calculations:

total flow rate: 133.3 ml/min
aorta pressure: 77.0 mmHg
arterial terminal pressure: 57.0 mmHg
right atrium pressure: 1.0 mmHg
venous terminal pressure: 5.0 mmHg
parameter $\alpha$ in $E_{med}$: $1.0 \times 10^{-3}$
parameter $\beta$ in $E_{med}$: $1.0 \times 10^3$
parameter $\eta$ in $f_{shrink}$: $1.0 \times 10^5$
radius-relationship parameter $\gamma$ of bifurcating vessels: 2.55
viscosity of blood: 4.0 cp The following description will now explain in detail the selection order of myocardial nodes, which has been mentioned at steps S123 and S124 of FIG. 16. The vessel generation process tends to produce large vessels in its early stage. If the selection of myocardial nodes is purely at random, the resulting coronary circulation model would lack some specific features of coronary circulation (e.g., larger vessels running on the myocardial surface). For this reason, the second embodiment preferably begins its node selection at the surface of the myocardium, rather than selecting nodes at random.

Figure 22:
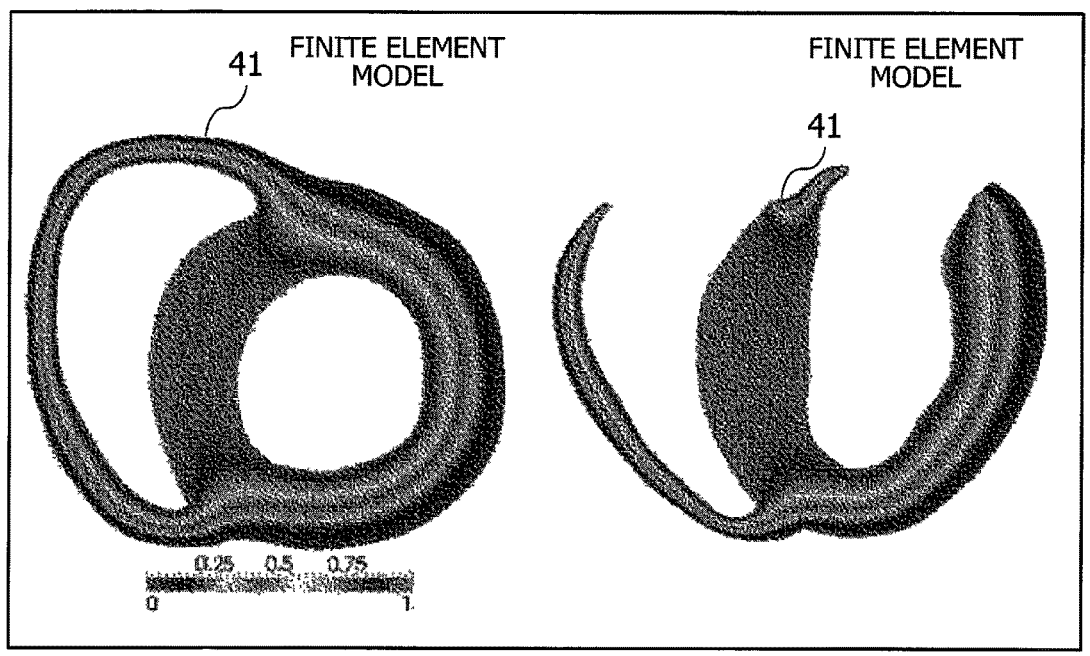
FIG. 22 schematically depicts exemplary solutions of the Laplace's equations.

The second embodiment uses solutions of Laplace's equations, with a boundary condition of zero for epicardium and one for endocardium. FIG. 22 schematically depicts exemplary solutions of Laplace's equations. Specifically, FIG. 22 uses texture patterns with varying tones to express how the solutions take larger values in the direction from epicardium to endocardium on the cross-section of the finite element model 41.

Now, let M represent the entire set of myocardial nodes, $M_u \subseteq M$ a set of myocardial nodes having no assignment of vessel end points, and $\Phi(m)$ the solution of Laplace's equation corresponding to each myocardial node $m \in M$. It is assumed that a pending myocardial node $m_u \in M_u$ is selected with a probability of $f_{select}$ given below.

$$f_{select}(m_u) = \frac{\exp\{-\kappa \phi(m_u)^2\}}{\sum_{n \in M_u} \exp\{-\kappa \phi(n)^2\}} \quad (18)$$

where coefficient $\kappa$ is a positive real number. The vessel generation process successively selects pending myocardial nodes at the probability $f_{select}$ given by the formula (18), thereby giving higher selection priorities to myocardial node close to the epicardium. As mentioned above, thicker vessels are produced at myocardial nodes that are selected earlier. The above-described distribution of selection probabilities makes it possible to produce a coronary circulation model that realizes the features of large vessels running on the myocardial surface.

The modeling process assigns a blood flow to each myocardial node to represent distribution of blood flows in the myocardium. Specifically, it is known that the myocardium exhibits a larger amount of blood flow on its endocardial side than on its epicardial side because the former has stronger contractions than the latter. The second embodiment therefore provides an algorithm for determining flow rates by using solutions of Laplace's equations similarly to the node selection algorithm discussed above. Specifically, this flow rate decision algorithm calculates a flow rate at each myocardial node, so that the blood flow densities on the endocardium and epicardium will have a ratio of 1:b, where b is a real number between zero and one exclusive. First, let $\Phi(m)$ represent the solution of Laplace's equation at a myocardial node $m \in M$, and $V_{node}(m)$ be the node volume at that node m. Each myocardial element (e.g., tetrahedron) has a particular volume, and this volume is divided by the number of vertices (or nodes) of the element. The divisor is four in the case of tetrahedral elements. The divided volumes are then distributed to each of these nodes, and the same calculations take place at every myocardial element. Finally every node has gained its "node volume," i.e., the sum of divided volumes contributed to a node by its surrounding elements. The flow rate decision algorithm now calculates the weighting coefficient W(m) of myocardial node m as follows.

$$w(m) = \frac{\{1 + (b-1)\phi(m)\} \cdot V_{node}(m)}{\sum_{n \in M} \{1 + (b-1)\phi(n)\} \cdot V_{node}(n)} \quad (19)$$

When the total blood flow $Q_{all}$ into the myocardium is given, the flow rate at node m is calculated to be $Q_{all} \times W(m)$.

The flow rate at each node is determined properly in terms of the anatomy, and those flow rate values are then used in calculation of parameters that characterize the vessel segments produced with the method based on optimal modeling. The resulting coronary circulation model is therefore precise from the anatomical viewpoint.

The coronary circulation modeling unit 120 adds the data of produced vessel segments to the macro model 143 in the storage unit 140. More specifically, the node data table 143a and vessel segment data table 143b are populated with additional data values that describe vessel segments produced with the optimal modeling-based method.

b4) Remove Zero-Flow Vessels

This subsection describes in detail a process of deleting zero-flow vessels, i.e., the vessels that have no assignment of blood flows. As described above, the second embodiment has produced an initial model from anatomical statistics data and then subjected it to a method based on optimal modeling to produce and connect additional vessels on the nodes of cardiac meshes, as well as calculating and assigning flow rates of blood. Some of the vessels in the initial model may remain in a zero-flow state. The second embodiment removes such vessels from the model as discussed in FIG. 13.

The removal of vessels is expected to eliminate unrealistic vessels in the model, such as those creeping over the inner wall or those bouncing back to the outer wall after reaching the inner wall. One of the roles of conduit vessels is to achieve efficient delivery of blood to the microcirculation system, and the minimum volume modeling is to construct an appropriate form of vessels that fulfill their roles. From this standpoint, a consistently thick blood vessel creeping over the inner wall of the heart is considered to be inefficient and thus unsuitable for the role of blood-supplying conduits. The optimal modeling-based method, including minimum volume modeling, adds no new vessel connections to such inefficient vessels. The second embodiment is therefore configured to remove unrealistic vessels that have gained no additional vessels.

The coronary circulation modeling unit 120 deletes the data of zero-flow vessel segments from the macro model 143 in the storage unit 140. More specifically, the node data table 143a and vessel segment data table 143b are updated to reflect the removal of those vessels. This means the completion of a macro model as part of the coronary circulation model.

Figure 23:
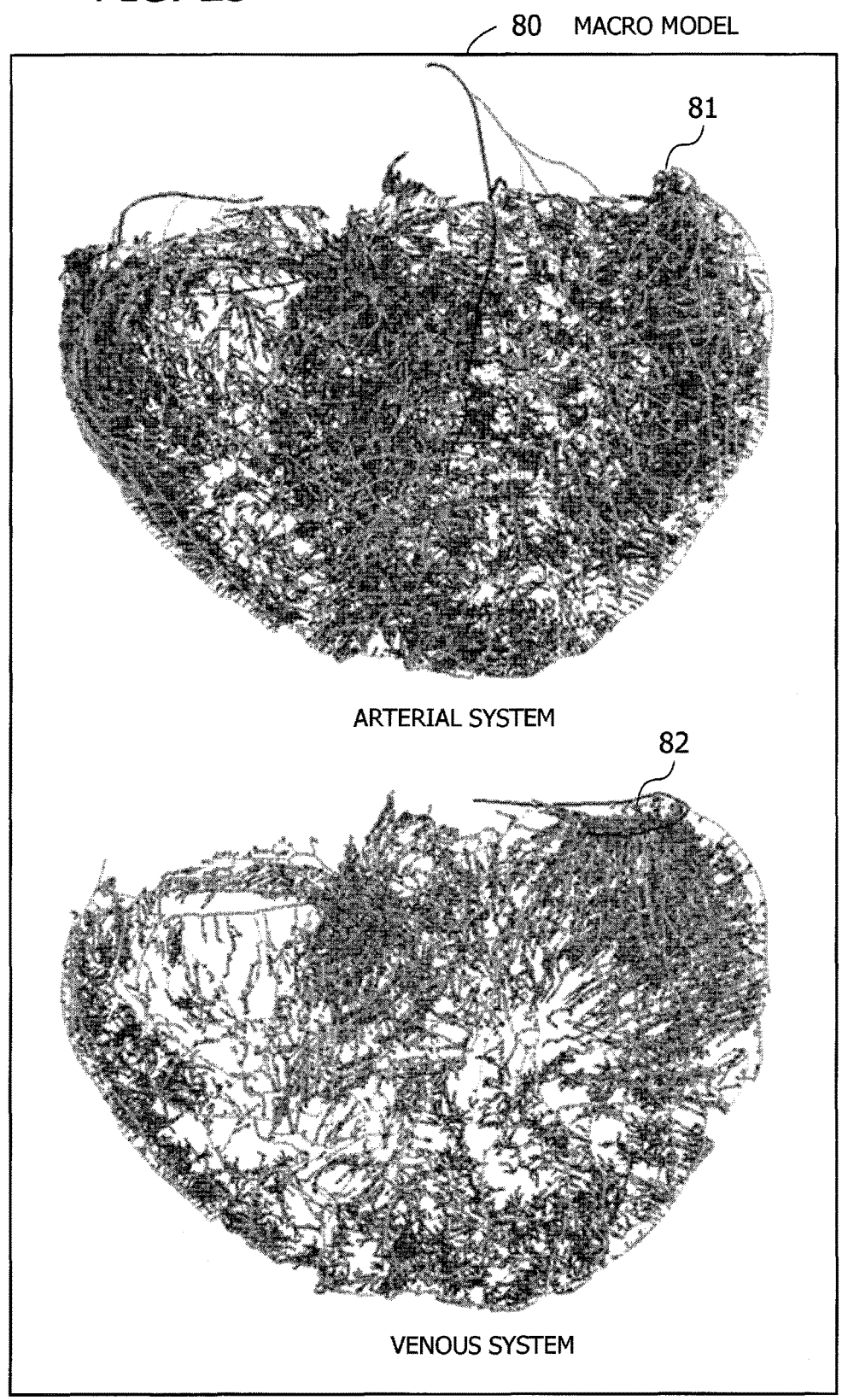
FIG. 23 illustrates an example of a produced macro model.

FIG. 23 illustrates an example of a produced macro model. This macro model 80 depicts a coronary circulation network in two separate parts, i.e., arterial system 81 and venous system 82.

The thickness and number of vessels produced with a method based on optimal modeling may vary depending on the setup of parameters and the resolution of finite element meshes. The parameters and mesh resolution are determined in consideration of multi-scale analysis in the coronary circulation simulation.

(c) Coronary Circulation Modeling (Micro Models)

Multi-scale analysis uses a coronary circulation model designed to deal with multiple vascular networks that fall into different scale ranges, from large coronary arteries and veins to small capillaries. In this coronary circulation model for multi-scale analysis, a large coronary artery originates in the aorta and branches out into smaller arteries, then into arterioles, and finally into capillaries. The capillaries then join and widen to become venules. The venules further join together to become veins and then to form a large coronary vein, which finally reaches the right atrium of the heart. This venous network is also part of the coronary circulation model.

Figure 24:
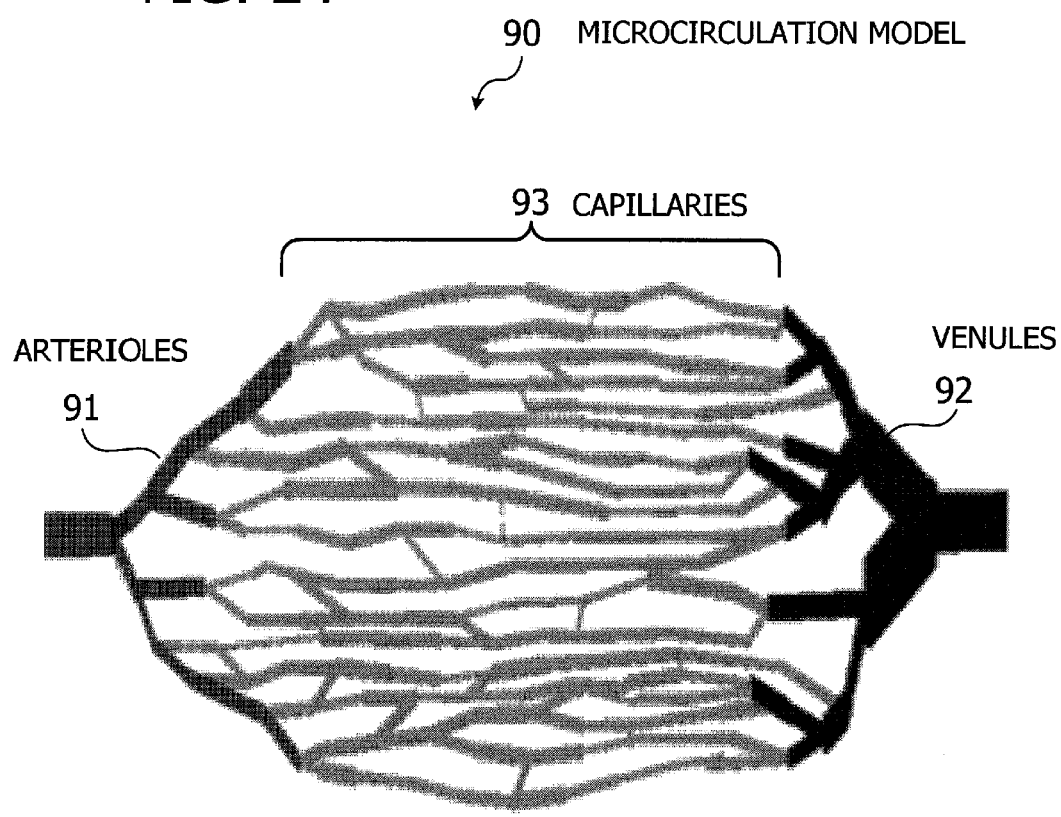
FIG. 24 illustrates an example of a microcirculation model.

FIG. 24 illustrates an example of a microcirculation model. The illustrated microcirculation model 90 is a representation of arterioles 91, venules 92, and capillaries 93, based on anatomical data. The second embodiment further produces intermediate models to represent vessels of intermediate scales between microcirculation models 90 and macro models 80, assuming their symmetry as will be seen in FIG. 25. These intermediate models play the role of connecting microcirculation models to the macro model 80, and the resulting combination of microcirculation models and intermediate models forms another class of vascular network model called "micro model." The implementation of symmetrical intermediate models permits a drastic reduction of computational load in the simulation, without losing inherent characteristics of the vascular network.

Figure 25:
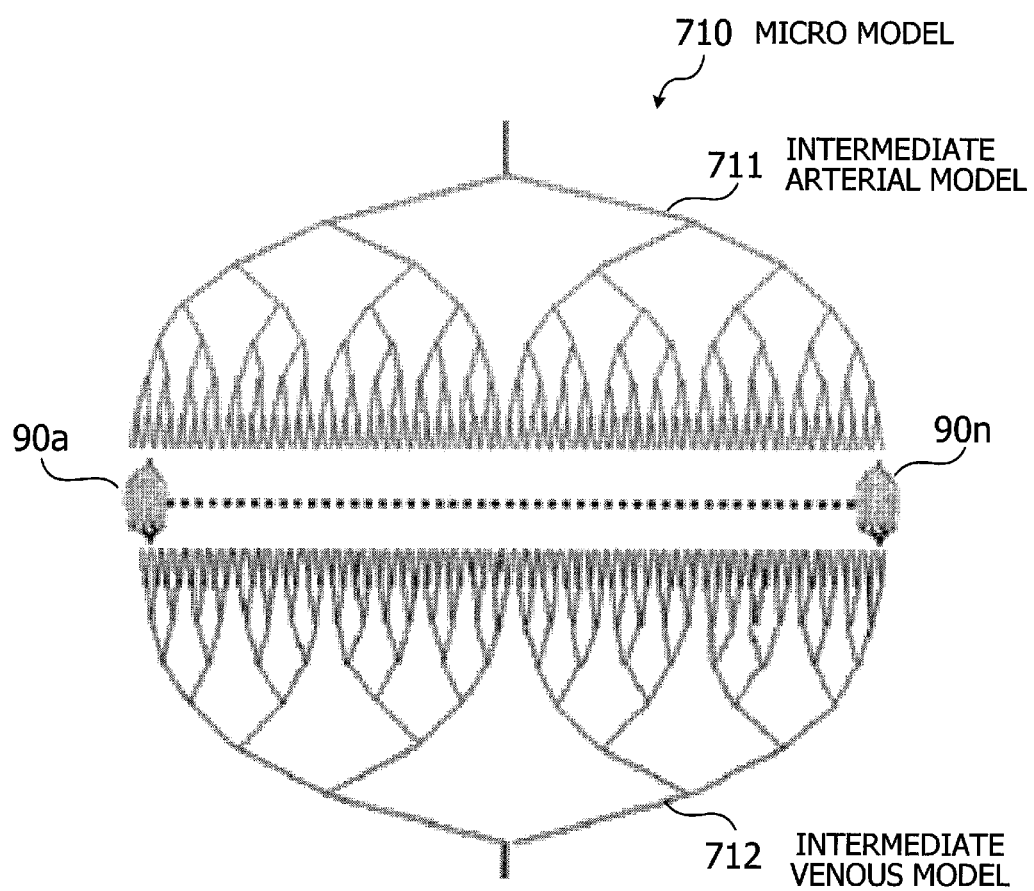
FIG. 25 illustrates an example of a micro model.

FIG. 25 illustrates an example of a micro model. The illustrated micro model 710 includes an intermediate arterial model 711, an intermediate venous model 712, and a plurality of microcirculation models 90a, . . . , 90n. The root of the intermediate arterial model 711 is connected to a large vessel model, while the end points of the same are connected to microcirculation models 90a to 90n. This is also true to the intermediate venous model 712.

It is assumed for coronary circulation simulation that each end point of a macro model meets several micro models at a pressure node k of the cardiac muscle. The micro models receive an external pressure from the cardiac muscle at pressure node k, which is referred to as a myocardial node pressure $P_k$. The number of micro models coupled to the pressure node k is determined from lumped myocardial node volume $V_k^{muscle}$. Further, each myocardial node is given a value of relative vessel density to take into consideration the dependency of the density of small vessels per myocardial volume on the transmurality (i.e., depth from the outer wall of the heart). Micro model vessel volume $\rho_k$ represents the volume of blood vessels contained in a unit volume at a pressure node k. This micro model vessel volume $\rho_k$ is calculated on the basis of the ratio of total volume of vessels in micro models to the cardiac volume. $V_{micro}$ represents the total volume of blood vessels in a single micro model. Now the following formula gives the number $n_k$ of micro models connected to a pressure node k at an end point of the macro model.

$$n_k = \frac{V_k^{muscle} \rho_k}{V^{micro}} \quad (20)$$

The following flow rate conservation law applies to each junction of arterial vessels and venous vessels in the macro model and micro models.

$$Q_{macro}^\delta + n_k Q_{micro}^\delta = 0 \quad (21)$$

where Q represents a flow rate. The subscript attached to Q indicates whether the flow rate is of macro models or of micro models. The superscript δ attached to Q indicates whether the flow rates is of arteries or of veins.

Figure 26:
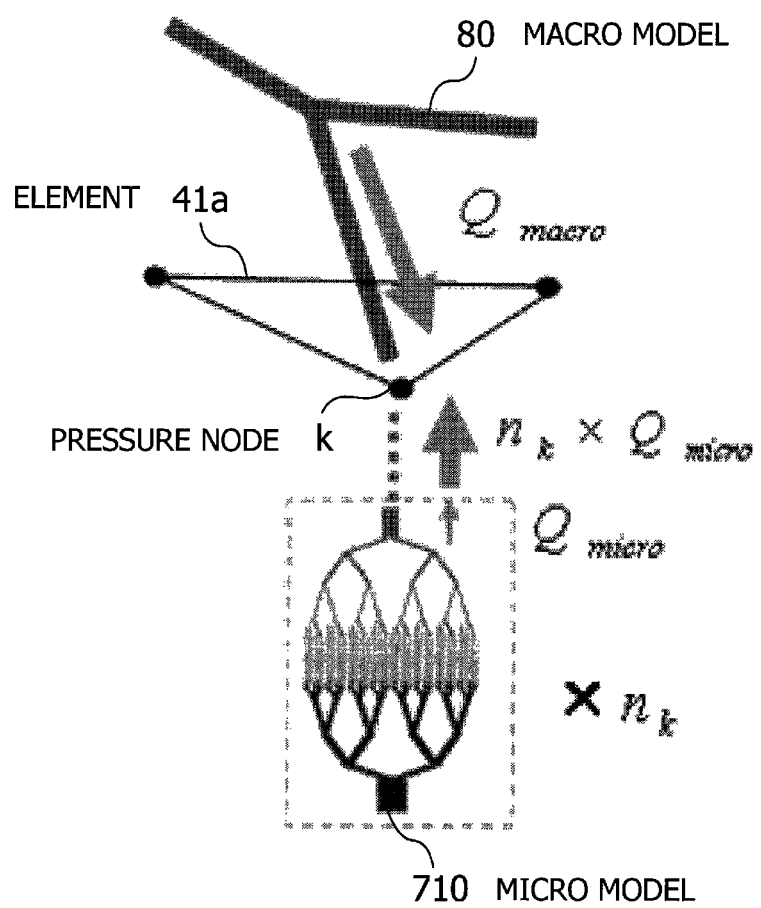
FIG. 26 illustrates how a macro model is connected to micro models via a pressure node.

FIG. 26 illustrates how a macro model is connected to micro models via a pressure node. Seen in the center of FIG. 26 is an element 41a of the finite element model, in the form of a polyhedron obtained by placing line segments to interconnect adjacent pressure nodes. This element 41a includes a pressure node k via which a plurality $n_k$ of micro models 710 are connected to the nearest vessel of the macro model 80. The vessel network seen as part of the macro model 80 of FIG. 26 is an arterial network.

Referring first to the macro mode side, the blood flow $Q^\delta_{macro}$ macro from the macro model 80 to the pressure node k is distributed across the $n_k$ micro models 710. Referring then to the micro model side, the blood flows $Q^\delta_{micro}$ from $n_k$ micro models 710 are combined into a vessel of the macro model 80 at the same pressure node k. The direction of blood flows is expressed in the sign of Q values. Specifically, $Q^\delta_{micro}$ micro takes a negative value when it represents a blood flow from a macro model 80 to micro models 710 as depicted in FIG. 26. The sum of the macro flow $Q^\delta_{macro}$ and $n_k$ times the micro flow $Q^\delta_{micro}$ is always zero as seen in equation (21).

The macro model 80 differs from micro models 710 in the diameter ranges of their vessels, the boundaries being drawn at about 100 μm. This fact has to be reflected in the selection of parameters and resolution of myocardial meshes for use in the optimal modeling-based method. That is, the parameters and mesh resolution are selected such that the resulting vascular network branches into terminal vessels with a diameter of about 100 μm.

The modeling process combines the macro model 80 with micro models 710 in this way, thus bringing the coronary circulation model to completion. The produced coronary circulation model is in good agreement with the anatomically known vascular networks.

Figure 27:
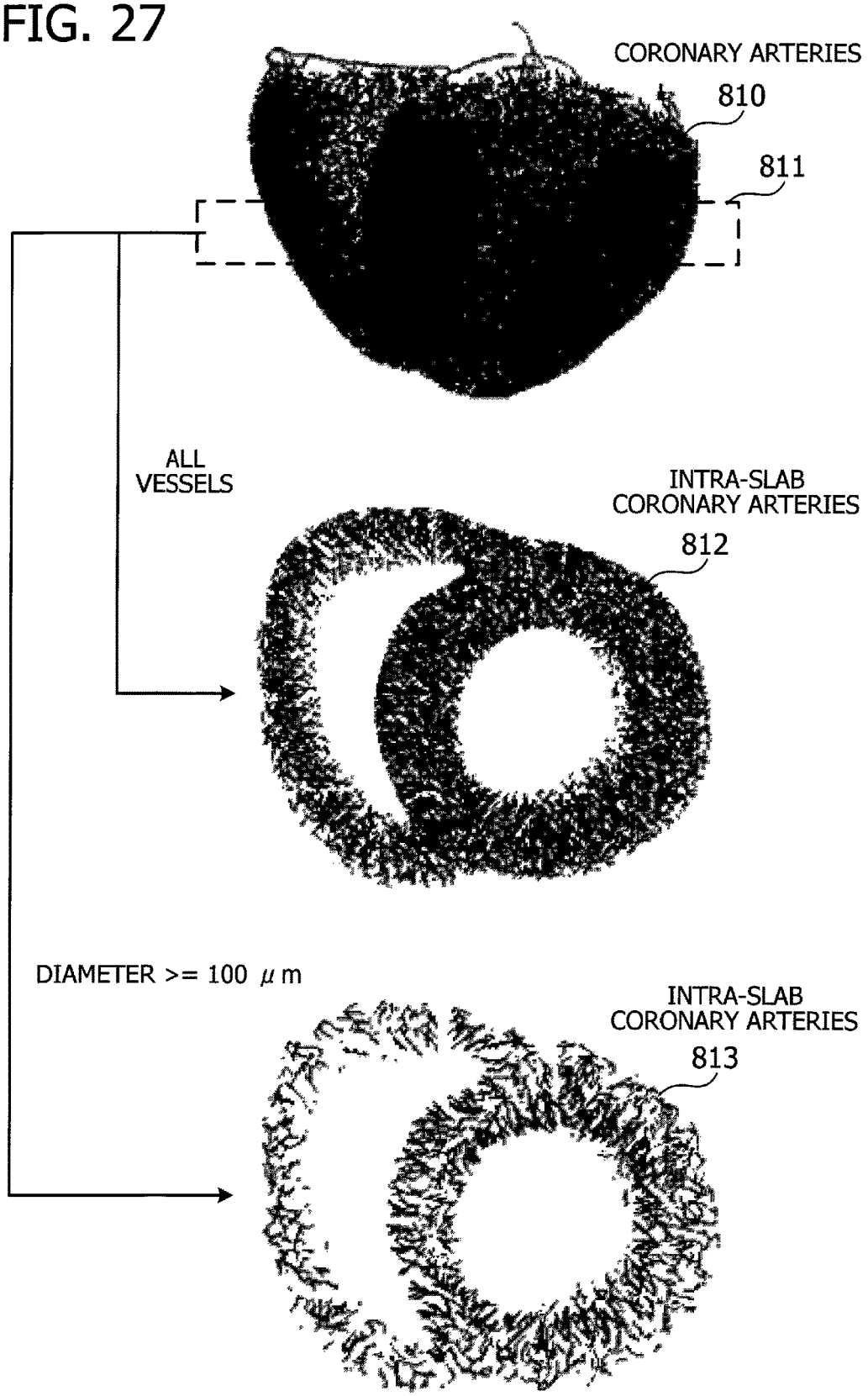
FIG. 27 illustrates an example of coronary arteries in a produced coronary circulation model.

FIG. 27 illustrates an example of coronary arteries in a produced coronary circulation model. Seen in the topmost section of FIG. 27 is the entire model of coronary arteries 810. A cross-sectional region on a transversal plane of the body is then extracted from the model. The extracted region is called a "slab region" 811, which contains coronary arteries referred to as "intra-slab coronary arteries." The middle section of FIG. 27 illustrates the entire set of intra-slab coronary arteries 812 contained in the slab region 811. Seen in the bottommost section of FIG. 27 are intra-slab coronary arteries 813 whose diameters are 100 μm or more.

Figure 28:
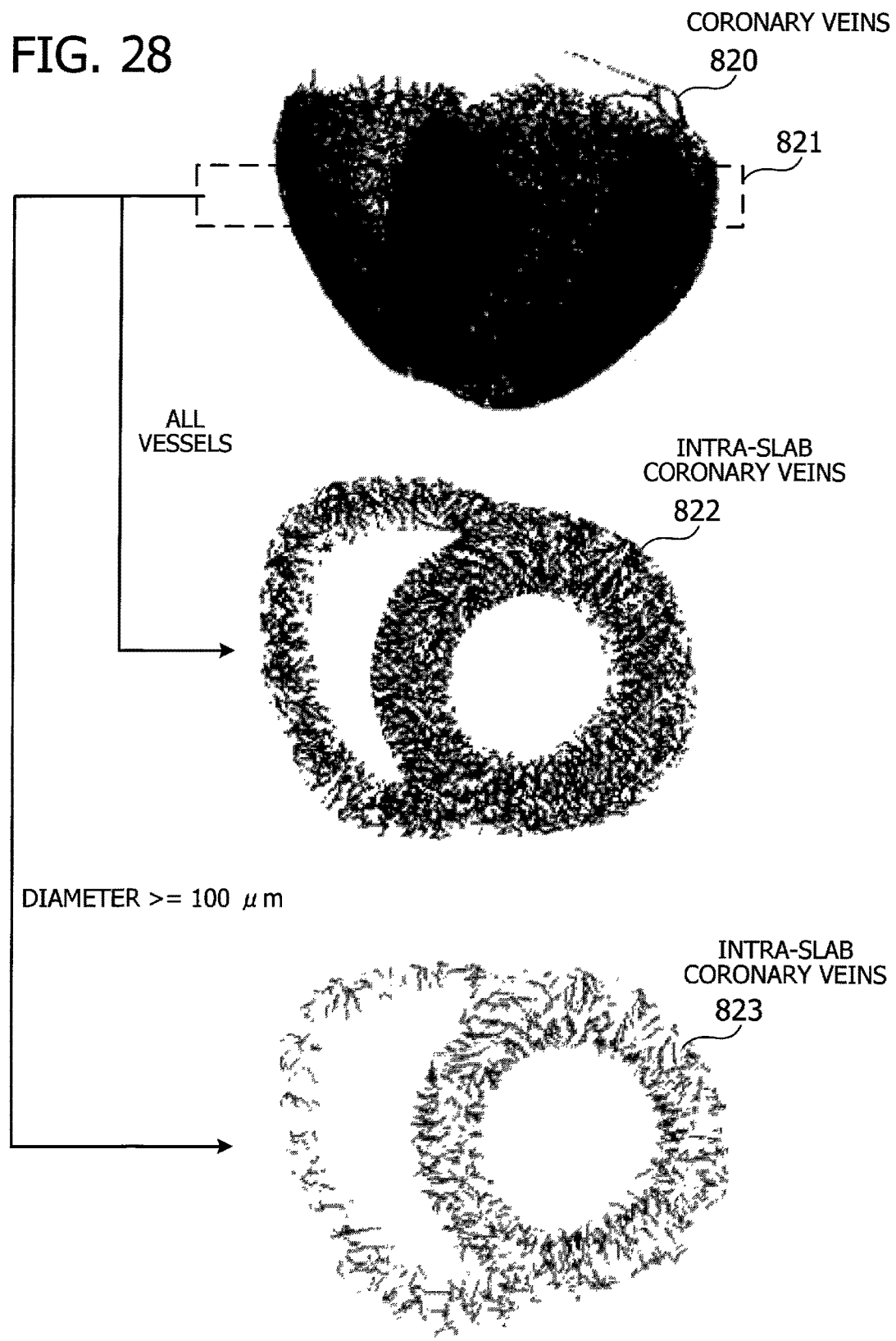
FIG. 28 illustrates an example of coronary veins in a produced coronary circulation model.

FIG. 28 illustrates an example of coronary veins in a produced coronary circulation model. Seen in the topmost section of FIG. 28 is the entire model of coronary veins 820. A slab region 821 on a transversal plane of the body contains coronary veins referred to as "intra-slab coronary veins." The middle section of FIG. 28 illustrates the entire set of intra-slab coronary veins 822 contained in the slab region 821. The bottommost section depicts intra-slab coronary veins 823 whose diameters are 100 μm or more.

The coronary circulation models of the second embodiment have been illustrated above in FIGS. 27 and 28. These models may be compared with coronary circulation models produced from anatomical statistics data alone. FIG. 29 illustrates an example of coronary circulation models produced for the purpose of comparison. Specifically, FIG. 29 illustrates intra-slab coronary arteries 910 and intra-slab coronary veins 920 in a coronary circulation model produced from anatomical statistics data alone. Referring to FIG. 29, the illustrated models have some vessels running on the inner wall as indicated by the white arrows. The same models also have some low-density regions as indicated by the hatched arrows. Referring back to FIGS. 27 and 28, the coronary circulation models of the second embodiment successfully reduced or eliminated the occurrence of such low-density regions and vessels running on the inner wall.

According to the second embodiment, the selection of myocardial nodes preferably begins at the surface of myocardium, rather than selecting nodes at random. This feature permits the modeling process to proceed from the outer surface of myocardium toward the endocardium.

FIG. 30 illustrates distribution of vessels of different orders. The upper half of FIG. 30 illustrates arteries 814 with an order of 7 or higher, which are a subset of the intra-slab coronary arteries. Similarly the lower half of FIG. 30 illustrates arteries 815 with an order of 6 or higher. The arteries 814 of order 7 or higher are distributed near the myocardial surface. The arteries 815 include order-6 arteries, which are thinner than order-7 arteries. These order-6 arteries are produced near the endocardium. That is, FIG. 30 indicates that the generation of vessels has proceeded in the direction from myocardial surface to endocardium.

The coronary circulation modeling unit 120 in the proposed CAD system 100 produces an anatomically faithful coronary circulation model in this way. The produced coronary circulation model includes a macro model 143 and a micro model 144, and they are stored in the storage device 300 as separate data.

(d) Simulation

Upon completion of a coronary circulation model, the simulation condition determination unit 130 submits simulation conditions to the managing node 200. In response, the managing node 200 causes a plurality of computing nodes 400, 500, 600, . . . to execute a coronary circulation simulation under the control of the same. For example, the managing node 200 first makes a copy of a finite element model 142, macro model 143, and micro model 144 from the storage unit 140 to the storage device 300. The managing node 200 then commands the computing nodes 400, 500, 600, . . . to start execution of a coronary circulation simulation.

For example, one computing node 400 executes macro model analysis, while the other computing nodes 500, 600 . . . perform micro model analysis in a distributed manner. The simulation is efficiently performed in this way, based on an anatomically faithful coronary circulation model, thus permitting the user to obtain reliable simulation results.

As can be seen from the above description, the second embodiment is configured to use a method based on optimal modeling produce vessel segments to produce vessel segments with their end points located at myocardial nodes. This feature prevents the resulting vascular network model from having poor-density regions.

The modeling process first produces a coronary circulation model by using a method based on anatomical statistics data. This vascular network contains some unrealistic vessels such as those creeping over the inner wall. The second embodiment is configured to trim the coronary circulation model by removing vessel segments that have gained no additional vessel segments. This feature prevents the coronary circulation model from including the unrealistic vessels noted above.

The source data for optimal modeling is produced on the basis of anatomical statistics data. This use of anatomical statistics data contributes to a better agreement of the resulting coronary circulation model with real observation results of the heart. For example, the model includes RCA and LCX running along the ventricle-atrium boundaries. Such vessels are difficult to reproduce in a model with the optimal modeling-based method alone.

The optimal modeling is used to produce additional vessel segments so as to minimize their energy. The second embodiment adds a special term $E_{med}$ to the energy so as to preserve measurement values used in the model. Coronary vessels modeled from medical images have their terminal blood pressures higher than the end-point pressures of vessel segments added to them. The noted feature of $E_{med}$ prevents the optimal modeling from violating this relationship of blood pressures.

The second embodiment also adds another special term $E_{shrink}$ to the energy so as to give a penalty to vessel shrinkage. This feature keeps the connection node of a new vessel segment away from existing end points of other vessel segments that share the connection node with the new segment.

As can be seen from the above, the second embodiment proposes several techniques for producing a coronary circulation model that is anatomically faithful. The use of a faithful model contributes to an enhanced reliability of simulation of coronary circulation.

The above sections have exemplified several embodiments. The components discussed in those embodiments may be replaced with other components having equivalent functions or may include some additional components or processing operations. Where appropriate, two or more components and features of the above-described embodiments may be combined in different ways.

In an aspect of the embodiment discussed above, the proposed techniques make it possible to provide a vascular network model that reproduces anatomical characteristics of an organ.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A vascular data generation apparatus comprising:
a memory storing anatomical data about a plurality of first vessels of a heart, a geometric model of the heart, and a program, the anatomical data representing a diameter and length of each of the plurality of first vessels of the heart and a branching structure of the plurality of first vessels of the heart; and
a processor coupled to the memory, the processor being configured to perform a procedure encoded in the program, the procedure including:
generating first vascular data based on the anatomical data, the first vascular data having a tree structure that represents a vascular network in the heart, the vascular network including the plurality of first vessels indicated in the anatomical data;
generating second vascular data representing a plurality of second vessels that connect a plurality of nodes in the geometric model of the heart with the vascular network represented by the first vascular data, the plurality of second vessels being generated without relying on the anatomical data; and
modifying the first vascular data by removing therefrom end portions of the vascular network that have no additional vessels connected in the second vascular data,
wherein the generating the second vascular data includes:
assigning a selection probability to each of the plurality of nodes in the geometric model, the selection probability of a node having a value that increases with a decrease in a distance from the node to an outer surface of the heart;
repeatedly selecting a connection node from unselected nodes among the plurality of nodes in the geometric model according to the selection probabilities of the unselected nodes; and
determining where to connect a new vessel produced at each of connection nodes in order of selection, as well as a length and a thickness of the new vessel.

2. The vascular data generation apparatus according to claim 1, wherein the generating the first vascular data includes:
connecting the first vessels indicated in the anatomical data to end points of vessels observed in medical images.

3. The vascular data generation apparatus according to claim 1, wherein the generating the second vascular data includes:
optimizing connection points at which the plurality of second vessels connects to the plurality of first vessels by using a predetermined evaluation function that gives a value depending on the connection points.

4. The vascular data generation apparatus according to claim 3, wherein:
the evaluation function is a function of a difference of blood pressures between one end point of the vascular network and an upstream point of a vessel connected to that end point;
when the upstream point has a higher blood pressure than the end point, the evaluation function increases the value as the difference of blood pressures between the end point and the upstream point becomes larger; and
when the upstream point has a lower blood pressure than the end point, the evaluation function decreases the value as the difference of blood pressures between the end point and the upstream point become larger.

5. The vascular data generation apparatus according to claim 3, wherein the evaluation function increases the value as the length of a vessel in the second vascular data gets longer than the diameter of the vessel.

6. The vascular data generation apparatus according to claim 3, wherein the evaluation function is a function of flow rates of blood in the plurality of first and second vessels, and the generating the second vascular data includes generating the flow rates of the blood in the plurality of first and second vessels, a flow rate of the blood in each of the plurality of first and second vessels having a value that increases with a decrease in a distance from a node to which the vessel is connected to an inner surface of the heart.

7. A method for producing vascular data, comprising:
storing anatomical data about a plurality of first vessels of a heart, a geometric model of the heart, and a program, the anatomical data representing a diameter and length of each of the plurality of first vessels of the heart and a branching structure of the plurality of first vessels of the heart to a memory;
generating, by a processor, first vascular data based on the anatomical data , the first vascular data having a tree structure that represents a vascular network in the heart, the vascular network including the plurality of first vessels indicated in the anatomical data;
generating, by the processor, second vascular data representing a plurality of second vessels that connect a plurality of nodes in the geometric model of the heart with the vascular network represented by the first vascular data, the plurality of second vessels being generated without relying on the anatomical data; and
modifying the first vascular data by removing therefrom end portions of the vascular network that have no additional vessels connected in the second vascular data,
wherein the generating the second vascular data includes:
assigning a selection probability to each of the plurality of nodes in the geometric model, the selection probability of a node having a value that increases with a decrease in a distance from the node to an outer surface of the heart;
repeatedly selecting a connection node from unselected nodes among the plurality of nodes in the geometric model according to the selection probabilities of the unselected nodes; and
determining where to connect a new vessel produced at each of connection nodes in order of selection, as well as a length and a thickness of the new vessel.

8. A non-transitory computer-readable medium storing a program, wherein the program causes a computer to perform a procedure comprising:
storing anatomical data about a plurality of first vessels of a heart, a geometric model of the heart, and a program, the anatomical data representing a diameter and length of each of the plurality of first vessels of the heart and a branching structure of the plurality of first vessels of the heart to a memory;
generating first vascular data based on the anatomical data, the first vascular data having a tree structure that represents a vascular network in the heart, the vascular network including the plurality of first vessels indicated in the anatomical data;

generating second vascular data representing a plurality of second vessels that connect a plurality of nodes in the geometric model of the heart with the vascular network represented by the first vascular data, the plurality of second vessels being generated without relying on the anatomical data; and modifying the first vascular data by removing therefrom end portions of the vascular network that have no additional vessels connected in the second vascular data, wherein the generating the second vascular data includes:
assigning a selection probability to each of the plurality of nodes in the geometric model, the selection probability of a node having a value that increases with a decrease in a distance from the node to an outer surface of the heart;
repeatedly selecting a connection node from unselected nodes among the plurality of nodes in the geometric model according to the selection probabilities of the unselected nodes; and
determining where to connect a new vessel produced at each of connection nodes in order of selection, as well as a length and a thickness of the new vessel.

* * * * *